US012806017B2

(12) United States Patent
Abunassar et al.

(10) Patent No.: US 12,806,017 B2
(45) Date of Patent: Nov. 24, 2026

(54) METHOD OF USE FOR VALVE REPAIR CLIP WITH AUTOMATIC LOCKING MECHANISM

(71) Applicant: Evalve, Inc., Santa Clara, CA (US)

(72) Inventors: Chad J. Abunassar, San Francisco, CA (US); David Strbjak, Munster, IN (US)

(73) Assignee: Evalve, Inc., Santa Clara, CA (US)

( * ) Notice: Subject to any disclaimer, the term of this patent is extended or adjusted under 35 U.S.C. 154(b) by 853 days.

(21) Appl. No.: 18/069,746

(22) Filed: Dec. 21, 2022

(65) Prior Publication Data

US 2024/0207050 A1 Jun. 27, 2024

(51) Int. Cl.
*A61F 2/24* (2006.01)

(52) U.S. Cl.
CPC .......... *A61F 2/2466* (2013.01); *A61F 2/2454* (2013.01)

(58) Field of Classification Search
CPC ....... A61F 2/2454; A61F 2/246; A61F 2/2466
See application file for complete search history.

(56) References Cited

U.S. PATENT DOCUMENTS 7,604,646 B2 10/2009 Goldfarb
7,635,329 B2 12/2009 Goldfarb
8,057,493 B2 11/2011 Goldfarb
9,011,468 B2 4/2015 Ketai
9,572,666 B2 2/2017 Basude
10,646,229 B2 5/2020 Goldfarb
11,484,331 B2 11/2022 Goldfarb
11,576,780 B2 2/2023 De Bonis
12,226,104 B2 2/2025 Zhang
2006/0020275 A1* 1/2006 Goldfarb ................ A61B 17/08 606/151
2007/0118155 A1 5/2007 Goldfarb
2010/0022823 A1 1/2010 Goldfarb
2013/0066342 A1 3/2013 Dell
2015/0257877 A1* 9/2015 Hernandez ......... A61B 17/0401 623/2.11
2018/0325671 A1 11/2018 Abunassar
2019/0000613 A1* 1/2019 Delgado .................. A61F 2/24
2019/0209323 A1 7/2019 Metchik (Continued)

FOREIGN PATENT DOCUMENTS

CN 106175845 B 1/2019
CN 111938870 A 11/2020

(Continued)

*Primary Examiner* — Leslie A Lopez
(74) *Attorney, Agent, or Firm* — SLEMAN & LUND LLP

(57) ABSTRACT

According to one aspect, a mitral valve clip is introduced using a delivery system. The clip includes two arms at an angle relative to one another and a lock that prevents widening of the angle when the angle is below a locking threshold value, wherein the lock is in a passively disengaged state when the angle is above the locking threshold value. The lock is manually disengaged and the angle is expanded to a leaflet capture starting angle. The lock is returned to the passively disengaged state after the angle is expanded to the leaflet capture starting angle. The leaflets of a mitral valve are captured while the lock remains in the passively disengaged state. The clip is closed to a final closure angle by narrowing the angle while the leaflets are trapped. The lock transitions to an engaged state when the angle falls below the locking threshold value.

20 Claims, 12 Drawing Sheets

(56) References Cited

U.S. PATENT DOCUMENTS

| | | | |
|---|---|---|---|
| 2019/0261995 | A1 | 8/2019 | Goldfarb |
| 2019/0314155 | A1 | 10/2019 | Franklin |
| 2020/0297482 | A1 | 9/2020 | Maimon |
| 2020/0360018 | A1 | 11/2020 | Dell |
| 2021/0093256 | A1 | 4/2021 | Troxler |
| 2021/0137680 | A1 | 5/2021 | Kizuka |
| 2021/0145574 | A1 | 5/2021 | Childs |
| 2021/0145583 | A1 | 5/2021 | Abunassar |
| 2021/0186698 | A1 | 6/2021 | Abunassar |
| 2021/0315695 | A1 | 10/2021 | Van Hoven |
| 2021/0393404 | A1 | 12/2021 | Ketai |
| 2022/0039943 | A1 | 2/2022 | Phan |
| 2022/0054132 | A1 | 2/2022 | Ketai |
| 2022/0117737 | A1 | 4/2022 | Abunassar |
| 2022/0142780 | A1 | 5/2022 | Zhang |
| 2022/0142781 | A1 | 5/2022 | Zhang |
| 2023/0157819 | A1 | 5/2023 | Zhang |
| 2023/0355390 | A1 | 11/2023 | Wang |
| 2024/0033084 | A1 | 2/2024 | Lv |
| 2024/0115386 | A1 | 4/2024 | Lv |
| 2024/0130858 | A1 | 4/2024 | Hu |
| 2024/0148505 | A1 | 5/2024 | Datta |
| 2024/0207050 | A1 | 6/2024 | Abunassar |
| 2024/0299169 | A1 | 9/2024 | Oberwise |
| 2024/0307184 | A1 | 9/2024 | Edwards |
| 2025/0009511 | A1 | 1/2025 | Abunassar |
| 2025/0120723 | A1 | 4/2025 | Huang |
| 2025/0160816 | A1 | 5/2025 | Basude |

FOREIGN PATENT DOCUMENTS

| | | | |
|---|---|---|---|
| CN | 109717987 | B | 6/2024 |
| EP | 4364695 | A1 | 5/2024 |
| WO | 2022081328 | A1 | 4/2022 |
| WO | 2023283368 | A1 | 1/2023 |

* cited by examiner

METHOD OF USE FOR VALVE REPAIR CLIP WITH AUTOMATIC LOCKING MECHANISM

BACKGROUND

Mitral valve regurgitation may be characterized by retrograde flow from the left ventricle of a heart through a compromised mitral valve into the left atrium. During a normal cycle of heart contraction (systole), the mitral valve ideally acts as a one-way valve to prevent flow of oxygenated blood back into the left atrium. In this way, the oxygenated blood is pumped into the aorta through the aortic valve. Valve regurgitation may significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

Common treatments for mitral valve regurgitation rely on valve replacement or repair including leaflet and annulus remodeling, the latter generally referred to as valve annuloplasty. Another technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

Alternatively, mitral valve regurgitation may be corrected by transcatheter delivery of an implant that facilitates full closure of the mitral valve during each heart contraction cycle. Transcatheter delivery can be a complicated process requiring close attention and many inputs and manipulations from an implanter, interventionalist, or physician, which will collectively be referred to with the term "physician" in the remainder of this disclosure. Some physicians may therefore find utility in a configuration of the implant and delivery system that requires relatively fewer inputs or manipulations throughout the delivery process.

BRIEF SUMMARY

According to an aspect of the disclosed technology, an assembly, which may be part of a mitral valve clip, includes a lock and a stud that may be movable relative to the lock. The stud may include a shank that may extend into the lock, and the lock may include a grip that can engage the shank to prevent movement of the stud relative to the lock in at least one direction. A portion of the shank may not be engageable by the stud. The grip may be unable to prevent movement of the stud in any direction relative to the lock by contact with the unengageable portion of the shank. If the grip is biased into contact with the unengageable portion of the shank, the grip may begin to prevent movement of the stud in at least one direction relative to the lock if the stud is moved until the grip contacts the engageable portion of the shank.

The engageable portion of the shank may have notches or a rough texture that the grip can engage frictionally or mechanically, and the unengageable portion of the shank may be too smooth for the grip to engage in a manner that would substantially impede movement of the stud relative to the lock in any direction. The grip may only prevent movement of the stud relative to the lock in one direction when engaged to the shank. The grip may be biased into contact with the shank by a force moment or a force along an oblique direction relative to a length of the shank such that force exerted on the grip in one direction along the length of the shank will counteract the bias force. A harness may extend into the lock in such a location that pulling the hook may manually counteract the bias force and move the grip out of contact with the shank.

According to another aspect of the disclosed technology, the lock and stud may be parts of a lockable mitral valve clip. The mitral valve clip may include two arms against which leaflets of the mitral valve may be anchored. The arms may be connected to the grip such that an angle between the arms is a function of the location of the stud relative to the lock. The arms may be pivotally connected to a frame of the lock, and each arm may be connected to a head of the stud by an bar extending between the arm and the head. The clip may be introduced into the heart through a catheter, the lock may be manually disengaged to spread the arms after introduction of the clip into the heart, and the lock may be permitted to automatically reengage the shank as the arms are brought together in a permanent configuration after the mitral valve leaflets have been anchored to the arms.

According to another aspect of the disclosed technology, a mitral valve clip may comprise a stud, a lock, and two arms. The stud may include a shank. The lock may include a frame relative to which the stud is translatable and into which the shank extends. The lock may be able to prevent movement of the stud relative to the lock in at least one direction by locking engagement of the shank. The two arms may be connected to the lock and the stud such that an angle between the arms depends on a location of the stud relative to the lock. The locking engagement of the shank that prevents movement of the stud relative to the lock in the at least one direction may only be possible when the angle between the arms is below 95°.

In another aspect of the disclosed technology, an assembly may comprise a stud and a lock. The stud may include a shank. The shank may have a rough-textured portion and a smooth portion aligned radially about a longitudinal axis of the shank with the rough-textured portion. The lock may include a frame into which the shank extends along the longitudinal axis, and a grip biased relative to the frame toward the longitudinal axis such that movement of the stud relative to the grip in at least one direction is prevented when the grip contacts the rough-textured portion of the shank, but movement of the stud relative to the grip is not restricted by the grip when the grip contacts only the smooth portion of the shank.

According to another aspect of the disclosed technology, a method of implanting a mitral valve clip may comprise introducing the mitral valve clip into a left atrium of a heart, the clip including two arms rotatable relative to one another and a lock that prevents widening of an angle between the arms when the lock is in an engaged state, and wherein the lock automatically transitions to the engaged state if the angle falls below a locking threshold while the lock is in a passively disengaged state. The method may also comprise manually disengaging the lock by applying force to a line extending out of the heart. The method may also comprise expanding the angle between the arms while the lock is manually disengaged, and permitting the lock to enter the passively disengaged state by releasing the force on the line after the expanding step. The method may also comprise capturing leaflets of the mitral valve by manipulating anchors of the clip and the arms to trap the leaflets of against the arms while the lock remains in the passively disengaged state, and closing the clip by narrowing the angle below the locking threshold while the leaflets are trapped against the arms by the anchors and the lock remains and without manually disengaging the lock.

One aspect of the disclosure is directed to a method for implanting a mitral valve clip. The method includes introducing the mitral valve clip into a left atrium of a heart using a delivery system, the clip including two arms at an angle relative to one another and a lock that prevents widening of the angle when the angle is below a locking threshold value, wherein the lock is in a passively disengaged state when the angle is above the locking threshold value; manually disengaging the lock and expanding the angle to a leaflet capture starting angle while the lock is manually disengaged; returning the lock to the passively disengaged state after the angle is expanded to the leaflet capture starting angle; capturing leaflets of a mitral valve by manipulating the clip to trap the leaflets while the lock remains in the passively disengaged state, and closing the clip to a final closure angle by narrowing the angle while the leaflets are trapped against the arms, wherein the lock transitions to an engaged state when the angle falls below the locking threshold value.

In some examples, the leaflet capture starting angle is about 90 degrees.

In some examples, the locking threshold value is about 60 degrees. As an alternative or addition, the locking threshold value may be about 45 degrees. As an alternative or addition, the locking threshold value may be between about 30 degrees to about 60 degrees.

In some examples, manually disengaging the lock is performed by applying tension to a harness line of the delivery system that extends to the lock. As an alternative or addition, returning the lock to the passively disengaged state may be performed by releasing the tension on the harness line.

In some examples, the clip is introduced into the left atrium with the angle at a smallest possible value.

In some examples, the method includes puncturing a hole in a wall of the left atrium, wherein the clip is introduced through the hole.

In some examples, manipulating the clip to trap the leaflets includes manipulating anchors of the clip to trap each leaflet against a respective anchor and a respective arm. As an alternative or addition, manipulating the anchors of the clips may include applying tension to one or more anchor lines of the delivery system.

In some examples, the final closure angle is between about 10 degrees and about 30 degrees.

In some examples, the method includes releasing the clip from the delivery system; and withdrawing the delivery system. As an alternative or addition, the lock may remain in the engaged state with the angle remaining at the final closure angle after the clip is released from the delivery system.

In some examples, the method includes making a second attempt to capture the leaflets, wherein making the second attempt includes manually disengaging the lock and expanding the angle up to the leaflet capture starting angle while the lock is manually disengaged.

DETAILED DESCRIPTION

When used in connection with devices for delivering a device into a patient, the terms "proximal" and "distal" are to be taken as relative to the user of the delivery devices. "Proximal" is to be understood as relatively close to the user, and "distal" is to be understood as relatively farther away from the user. As used herein, the terms "substantially," "generally," "approximately," and "about" are intended to mean that slight deviations from absolute are included within the scope of the term so modified.

In accordance with different aspects of the technology disclosed herein, a device is disclosed for use in valve repairs that may automatically transition from an unlocked state to a locked state when the device is closed to within a predetermined angle. For example, the device may comprise a mitral valve clip that comprises a threaded stud component that automatically transitions the clip from an unlocked state to a locked state when the clip is closed to a clip arm angle of approximately 60 degrees. This may be accomplished by modifying the threaded stud component to include a surface roughness change along the stud, which effectively allows the clip lock to be inactive at clip arm angles larger than, for example, 60 degrees and automatically active at clip arm angles less than 60 degrees. More generally, the value of the angle may be within a range suitable for visualizing the clip, positioning the clip, crossing the valve, and grasping and capturing the leaflets. In this way, a user may operate the clip through most steps involved in a repair procedure without having to closely monitor the state of the lock, which then automatically activates when the clip effectively closed onto the leaflets. The automatic locking mechanism may be accomplished by one or more of the multiple designs discussed below, including a shortened threaded stud design and shortened rough region design.

Figure 1:
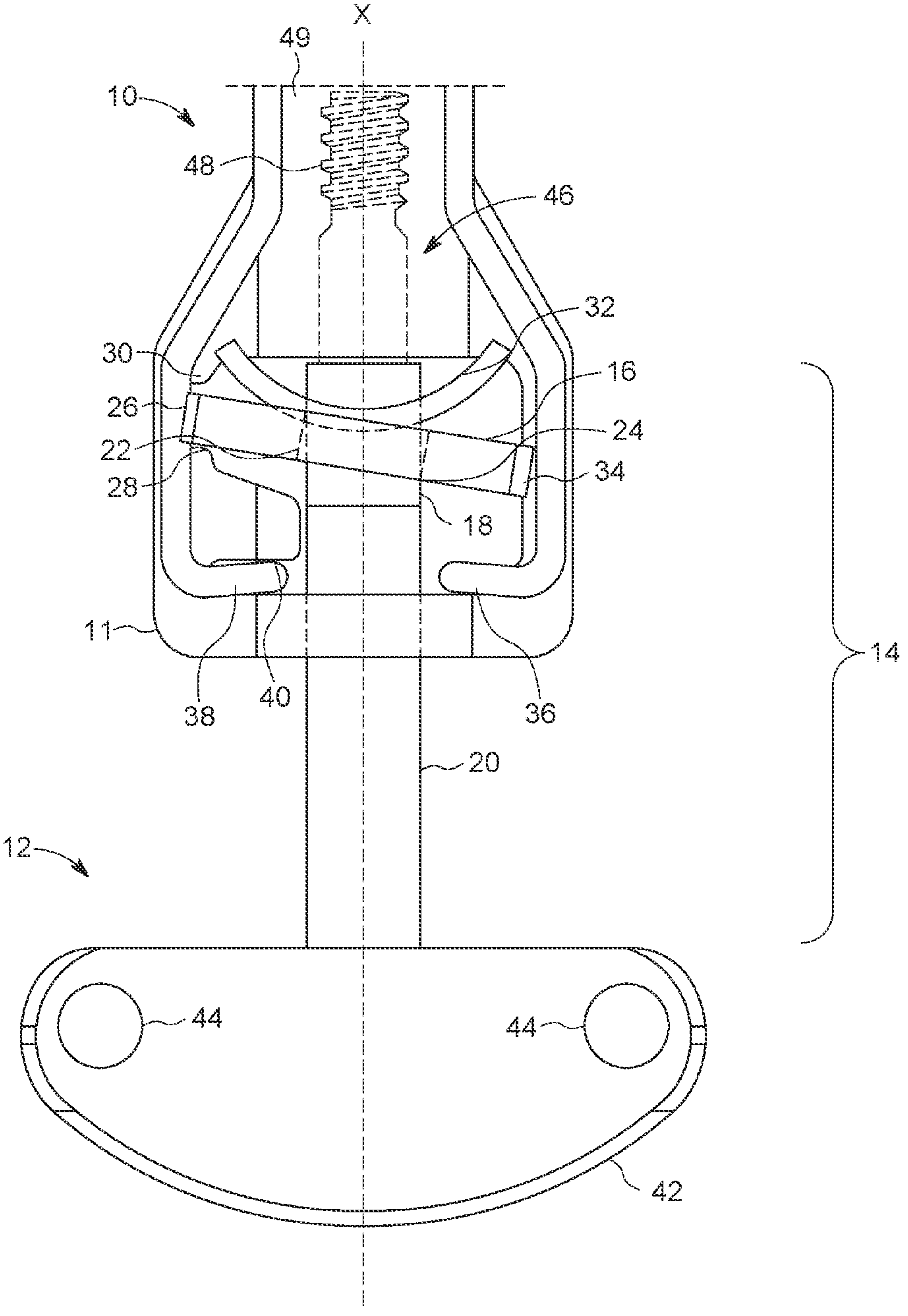
FIG. 1 is a front plan view of a lock and stud according to an example.

FIG. 1 illustrates a locking mechanism or lock 10 through which a stud 12 is translatable along a longitudinal axis X. From the perspective of FIG. 1, a proximal direction is upward along longitudinal axis X, while a distal direction is downward along the longitudinal axis. Lock 10 includes a grip 16 biased into contact with a longitudinally extending shank 14 of stud 12. Any grip within this disclosure may also be referred to as a pawl or tumbler, and in various examples may be formed in any shape commonly associated with pawls or tumblers. When grip 16 engages shank 14, grip 16 may restrict or prevent stud 12 from translating in at least one direction along longitudinal axis X. Shank 14 includes an unengageable portion 18 and an engageable portion 20, the engageable portion being distal of the unengageable portion. Grip 16 may therefore only engage shank 14 when the shank is located proximally enough for the grip to contact engageable portion 20. Lock 10 therefore limits translation of stud 12 when the stud is within a certain range of axial positions relative to the lock, but a range of axial positions exists wherein the stud is free to translate. The following details and corresponding features illustrated in FIG. 1 are one example of how a lock may selectively limit axial translation of a stud when the stud is within a certain range of axial positions relative to the lock, though such features are possible with other arrangements and structures.

In the illustrated example, grip 16 is a binding plate including a channel 22 through which shank 14 extends. In other examples, grip 16 may be a pawl or tumbler. Grip 16 has a pivot end 26 which is trapped between a distal protrusion 28 and a proximal protrusion 30 of a frame 11 of lock 10. Pivot end 26 thus has little or no room to translate and acts as a pivot point about which grip 16 may rotate. Grip 16 also includes a free end 34 on an opposite side of channel 22 and longitudinal axis X from pivot end 26. As grip 16 rotates about pivot end 26, channel 22 and free end 34 therefore change angular position relative to the pivot end at the same rate and in the same direction.

A spring 32, which may take the form of a resiliently flexible disc or a leaf spring as indicated in the illustrated example, is trapped in a compressed state within lock 10 between a distal-facing surface of frame 11 and a proximal facing surface of grip 16. Spring 32 is therefore located proximally of its point of contact on grip 16 and biases the grip 16 distally. Because movement of grip 16 is constrained mostly or entirely to rotating about pivot end 26, which is to the left of the contact point between spring 32 and the grip from the perspective of FIG. 1, the distal bias from the spring causes the grip overall to be biased toward rotation in a clockwise direction from the perspective of FIG. 1. Because grip 16 extends distally and across longitudinal axis X from pivot end 26, a biting edge 24, which is a corner at a distal end of channel 22 of the grip opposite from the pivot end, is biased into contact with shank 14. Biting edge 24 is a sharp edge or textured surface suitable for engaging the surface of engageable portion 20 such that bias of the biting edge 24 onto the engageable portion may prevent axial travel of stud 12 in at least one direction relative to grip 16 when the stud is subject to forces within the magnitudes typically exerted upon the stud as part of any application in which lock 10 is used.

As noted above, shank 14 includes unengageable portion 18 and engageable portion 20. Biting edge 24 of grip 16 can engage engageable portion 20, but cannot engage unengageable portion 18. For example, engageable portion 20 may have a rough texture or a finish otherwise conducive to friction with biting edge 24, which may be textured or sharp, while unengageable portion 18 may be smooth or otherwise finished in a way that minimizes friction with the biting edge. In other examples, engageable portion 20 may have, and unengageable portion 18 may lack, any other feature engageable by grip 16 such that axial movement of stud 12 would be restricted when the grip engages those features. For example, engageable portion 20 may have a series of notches in which biting edge 24 may be received, and such notches may be absent from unengageable portion 18. Unengageable portion 18 of shank 14 may also be slightly smaller in diameter than engageable portion 20 such that interactions between grip 16 and the unengageable portion are further minimized. A chamfer may be provided at the transition between unengageable portion 18 and engageable portion 20 in examples where the two portions differ in diameter. An example chamfer is described in greater detail hereinafter with respect to FIG. 8.

Suitable roughness for unengageable portion 18 when lock 10 is applied as part of a mitral valve clip as described further below may be, for example, 0.150 micron arithmetic roughness or less, with some examples being from 0.05 to 0.150, or equal to or about 0.1, 0.11, or 0.12 micron arithmetic roughness. Suitable roughness for engageable portion may be, for example, 0.25 micron arithmetic roughness or more, with some specific examples being from 0.25 to 0.8, or equal to or about 0.55, 0.65, or 0.75 micron arithmetic roughness. The foregoing arithmetic roughness values may be applied in any example according to the current disclosure wherein a relatively rough texture enables engagement of an engageable portion of a stud and a relatively smooth texture prevents engagement of an unengageable portion of the stud, such as unengageable portion 18 and engageable portion 20 of stud 12 as illustrated in FIG. 1.

When grip 16 engages shank 14 by contact between biting edge 24 and engageable portion 20, axial movement of stud 12 is restricted, such as by friction between the biting edge and the engageable portion. However, when grip 16 does not engage shank 14, such as when biting edge 24 contacts unengageable portion 18, the biting edge will slide freely along unengageable portion so that stud 12 may translate axially absent some external constraint. Biting edge 24 of grip 16 therefore only acts to restrict axial movement of stud 12 when the stud is within a range of axial positions wherein the biting edge may contact engageable portion 20. Lock 10 is thus in an engaged state when biting edge 24 contacts engageable portion 20 with enough force to prevent axial movement of stud 12 in at least one direction relative to the lock, and the lock is in a passively disengaged state when the grip contacts only unengageable portion 18 or any tool engaged to a proximal end of shank 14. Lock 10 transitions from the passively disengaged state to the engaged state when stud 12 travels far enough proximally relative to the lock that biting edge 24 engages engageable portion 20 of shank 14.

In the illustrated example, grip 16 only restricts axial movement of stud 12 in one direction when biting edge 24 engages shank 14. Biting edge 24 is biased distally and, from the perspective of FIG. 1, left. Biasing is not limited to a given orientation but may tailored based on the design to be oriented to the right, for example, of FIG. 1. Because biting edge 24 contacts an axially extending surface of shank 14, friction between the biting edge and the shank is proportional to the leftward component of the force on the biting edge. Thus, when biting edge 24 engages engageable portion 20 of shank 14, distal impetus upon stud 12 will pull the biting edge distally, thereby creating a clockwise moment on grip 16 about pivot end 26 that cooperates with spring 32 bias to increase the leftward force of the biting edge on the shank. Friction between grip 16 and engageable portion 20 therefore increases when distal force exists upon stud 12. As a result, stud 12 is prevented, or at least significantly inhibited, from travelling distally relative to lock 10 when grip 16 engages engageable portion 20 of shank 14. However, when biting edge 24 engages engageable portion 20 of shank 14, proximal impetus upon stud 12 will push the biting edge proximally, counteracting the clockwise moment on grip 16 created by spring 32 bias and reducing the leftward force of the biting edge on the shank. Friction between grip 16 and engageable portion 20 therefore decreases when proximal force exists upon stud 12. As a result, engagement between grip 16 and engageable portion 20 does not prevent proximal travel of stud 12 relative to lock. Thus, through engagement of engageable portion 20 of shank 14 by grip 16, lock 10 restricts movement of stud 12 by inhibiting or preventing the stud from moving distally relative to the lock. The foregoing is one example of how a lock may unidirectionally restrict travel of a stud, though such restriction may be accomplished with other mechanics in other examples.

The above described interaction between grip 16 and shank 14 creates a system wherein stud 12 may be translated either proximally or distally without restriction caused by the grip 16 as long as biting edge 24 remains aligned along longitudinal axis X with unengageable portion 18 or is proximal of the unengageable portion, and wherein the stud may be translated only proximally relative to frame 11 after engageable portion 20 reaches biting edge 24 until spring 32 is counteracted to disengage the grip from the shank. When biasing force between grip 16 and frame 11, such as by spring 32, is counteracted such that the grip cannot contact shank 14, lock 10 is in an actively or manually disengaged state.

First hook 36 is an example of a mechanism that may counteract spring 32 to actively or manually disengage grip 16 from engageable portion 20 of shank 14. First hook 36 may be pulled proximally to catch free end 34 of grip 16 to counteract spring 32 and move biting edge 24 away from shank 14. First hook 36 may be biased distally such that, in the absence of input from a user, the first hook does not interfere with clockwise rotation of grip 16. In the illustrated example, first hook 36 is connected to a second hook 38 by a resiliently flexible wire that is not visible in FIG. 1 to form a harness. Because the wire is resiliently flexible, pulling proximally on the wire may move first hook 36 proximally while second hook 38 is restrained by shelf 40 of frame 11, and upon release of proximal tension the wire will return toward a rest shape wherein the first hook does not interfere with clockwise rotation of grip 16. However, this interaction between first hook 36 and second hook 38 is merely exemplary, and first hook 36 may be biased by other mechanics, such as a linear spring arrangement, or other structures may be used to selectively disengage grip 16.

Stud 12 of the illustrated example includes a head 42 at its distal end and a plug 46 at its proximal end. Head 42 includes holes 44 and plug 46 includes external threads 48. Stud 12 therefore includes features by which other apparatus may be coupled to its proximal or distal ends, though such features may be different in other examples. The above described selective restriction of movement between stud 12 and lock 10 may therefore be used to selectively restrict movement of apparatus coupled to either end of the stud and frame 11 of the lock or apparatus coupled to the frame. For example, frame 11 of the illustrated example includes proximal sleeve 49 into which plug 46 extends, and the sleeve may include coupling features, such as a hook at its proximal end or a through-hole, not visible in FIG. 1. The relative proportions of unengageable portion 18 and engageable portion 20 of shank 14 dictates the extent of the range of axial positions relative to lock 10 wherein stud 12 and apparatus coupled thereto can translate axially without restriction and the extent of the range of axial positions relative to the lock wherein axial translation of the stud and apparatus coupled thereto is restricted in at least one direction.

Figure 2A:
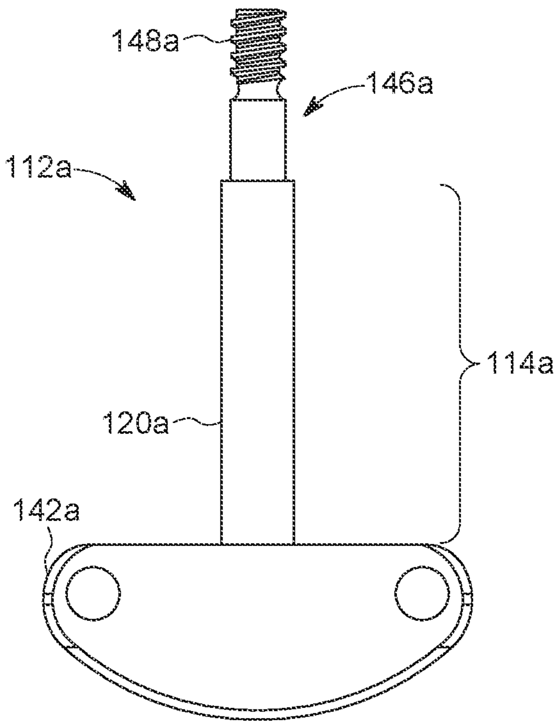
FIGS. 2A-2D are front elevation views of studs usable with the lock of FIG. 1 according to certain examples.
Figure 2B:
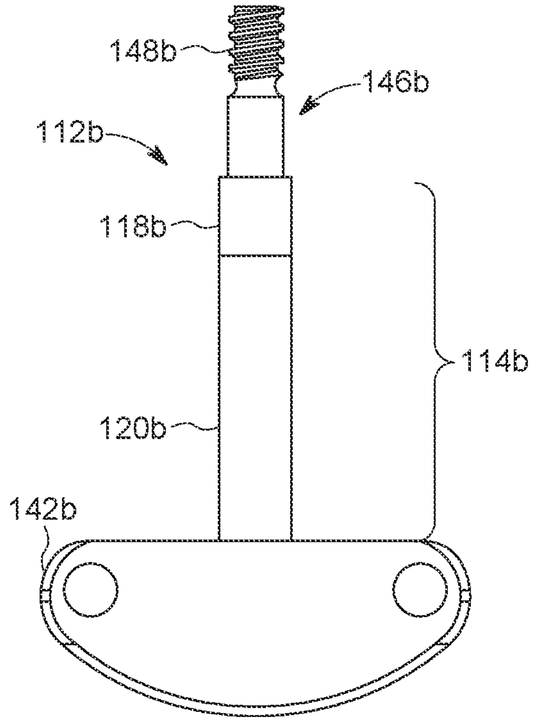
Figure 2C:
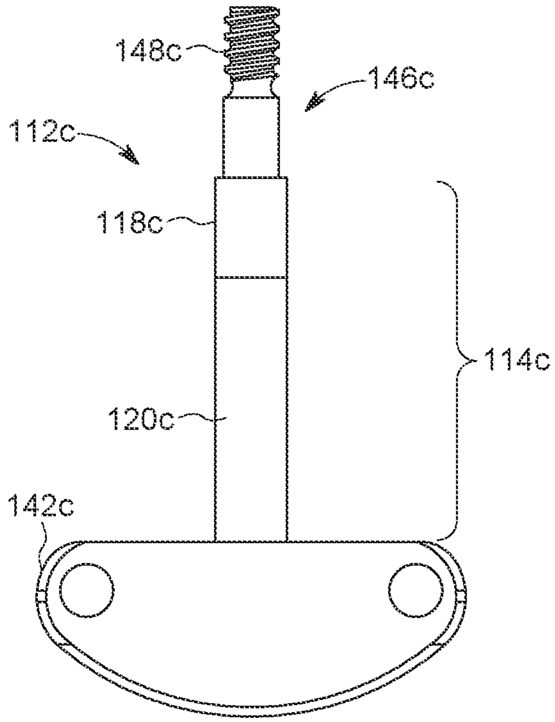
Figure 2D:
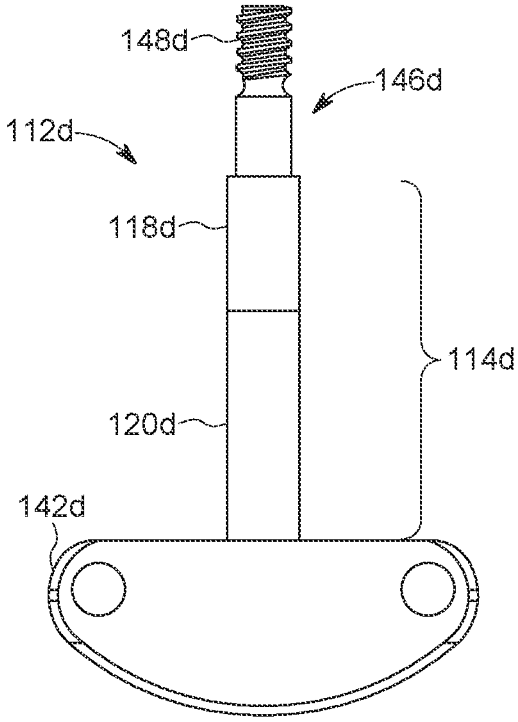

FIGS. 2A-2D illustrate studs **112*a*, 112*b*, 112*c*, 112*d*, which may be used in lock 10 of FIG. 1, having different length ratios between unengageable portions 118*b*, 118*c*, 118*d* and engageable portions 120*a*, 120*b*, 120*c*, 120*d* of their respective shanks 114*a*, 114*b*, 114*c*, 114*d*. Similar to stud 12 of FIG. 1, each stud 112*a*, 112*b*, 112*c*, 112*d* has a respective head 142*a*, 142*b*, 142*c*, 142*d* at a distal end of the respective shank 114*a*, 114*b*, 114*c*, 114*d* and a plug 146*a*, 146*b*, 146*c*, 146*d* having a threaded portion 148*a*, 148*b*, 148*c*, 148*d* at a proximal end of the respective shank. Shank 114*a* of stud 112*a* of FIG. 2A includes no unengageable portion, meaning engageable portion 120*a* extends an entire length of shank 114*a*. If stud 112*a* of FIG. 2A were disposed axially through lock 10 in the same manner as stud 12, grip 16 could therefore restrict axial movement of stud 112*a* when stud 112*a* was at any axial position wherein biting edge 24 would contact shank 114*a*. Turning to FIGS. 2B, 2C, and 2D, engageable portion 118*b* provides equal to or about 79% of shank 114*b*, engageable portion 118*c* provides equal to or about 72% of shank 114*c*, and engageable portion 118*d* provides equal to or about 65% of a length of shank 114*d*, and engageable portions 120*b*, 120*c*, 120*d* each provide a remainder of the length of their respective shanks. As such, if shanks 114*a*, 114*b*, 114*c*, 114*d* are each assumed to be equal in length, they each enable unrestricted axial travel by their respective studs 112*a*, 112*b*, 112*c*, 112*d* within lock 10 across different ranges of axial locations of the respective stud relative to the lock. The illustrated proportions between unengageable portions 118*b*, 118*c*, 118*d* and engageable portions 120*b*, 120*c*, 120*d*** in FIGS. 2B, 2C, and 2D are merely examples, and it is possible for the unengageable portion of a shank to extend across any amount greater than 0% and less than 100% of a length of the shank.

The differing proportions of unengageable portions **118*b*, 118*c*, and 118*d* to engageable portions 120*a*, 120*b*, 120*c*, 120*d* may be produced by, for example, machining a smooth shank to have a smooth surface and then roughening only a portion of the surface, such as by blasting the shank while a proximal portion of the shank is shielded. Alternatively, the shank may be produced with a rough finish, such as by casting, and a proximal portion of the shank may be smoothed by, for example, machining. To enhance the unengageable nature of unengageable portion 18 of the shank, the diameter about longitudinal axis X of sections 118*b*, 118*c*, and 118*d* may be less than the diameter of corresponding engageable sections 120*b*, 120*c*, 120*d*. A chamfer transition may exist between the engageable portion and the unengageable portion of any of shanks 114*a*, 114*b*, 114*c*, 114*d* so that grip 16** acts smoothly without catching on the shank at the border between the unengageable and engageable portions.

Figure 8:
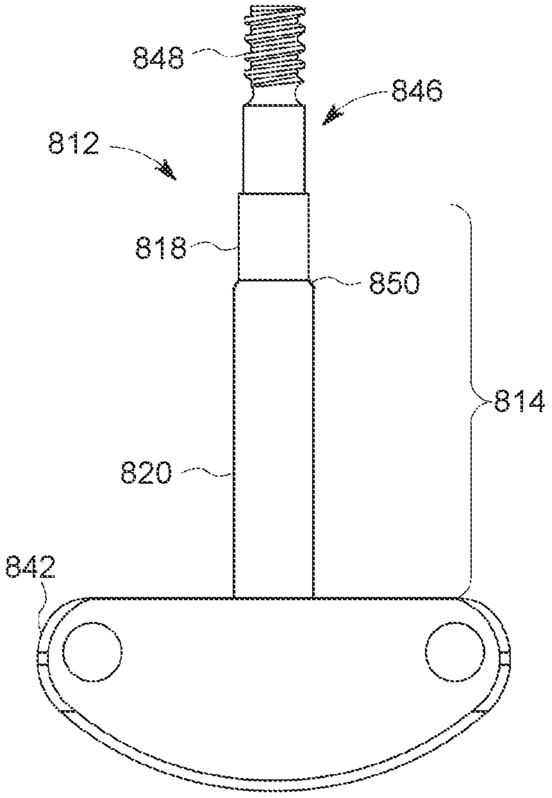
FIG. 8 is a front elevation view of a stud usable with the lock of FIG. 1 according to further examples.

FIG. 8 illustrates a front elevation view of a stud 812 according to another example that may be used in lock 10 of FIG. 1 according to further examples. One or more properties of stud 812 may be combined with one or more other examples described herein. The stud 812 has an unengageable portion 818 and an engageable portion 820. Similar to stud 12 of FIG. 1, the stud 812 has a head 842 at a distal end of a shank 814 and a plug 846 having a threaded portion 848 at a proximal end of the shank 814. The diameter of the unengageable portion 818 of the shank 814 is less than the diameter of the engageable portion 820. The reduced diameter of the unengageable portion 818 may reduce resistance of the grip 16 when the mitral valve clip is opened while the locking mechanism is in an engaged state, thereby reducing the force required to open the mitral valve clip and/or reducing a likelihood of the grip 16 catching when the mitral valve clip is opened.

In some examples, an outer diameter of the engageable portion 820 is about 0.0270 inches. As an alternative or addition, the outer diameter of the engageable portion 820 may have a tolerance of +0.00002 inches and −0.0003 inches. The shank 814 may have a chamfer transition 850 between the unengageable portion 818 and the engageable portion 820 such that the grip 16 acts smoothly without catching on the shank 814 at the transition between the unengageable portion 818 and the engageable portion 820. In examples, the chamfer transition 850 has an angle of about 45 degrees. As alternative or addition, the chamfer transition 850 may have an edge break of about 0.0005 inches. It should be understood that the specific dimensions provided above are merely exemplary, and other dimensions may be suitable.

In the illustrated examples of FIGS. 1, 2B-2D, and 8, boundaries or borders between engageable portions 18, 118*b*, 118*c*, 118*d*, 818 and unengageable portions 20, 120*b*, 120*c*, 120*d*, 820 may lie on a plane normal to axial lengths of their respective shanks 14, 114*b*, 114*c*, 114*d*, 814. In other examples, boundaries or borders between engageable portions 18, 118*b*, 118*c*, 118*d*, 818 and unengageable portions 120, 120*b*, 120*c*, 120*d*, 820 may extend at different angles, such as, for example, an angle matching or approximating an angle at which grip 16 would extend across shank 14, 114*b*, 114*c*, 114*d*, 814 when the respective stud 12, 112*b*, 112*c*, 112*d*, 812 is disposed through lock 10 and the grip is biased into contact with the shank. If grip 16 is configured to contact shank 12, 112*b*, 112*c*, 112*d*, 812 at multiple points, the boundary between the engageable portion and unengageable portion may be angled or even curved to match or approximate a slope along which the points lie. Grip 16 would then transition from unengaged to engaged in a binary or nearly binary manner as the respective stud travels proximally, with little or no potential for the grip to simultaneously contact the engageable and unengageable portions on opposite sides of a shank.

Figure 3A:
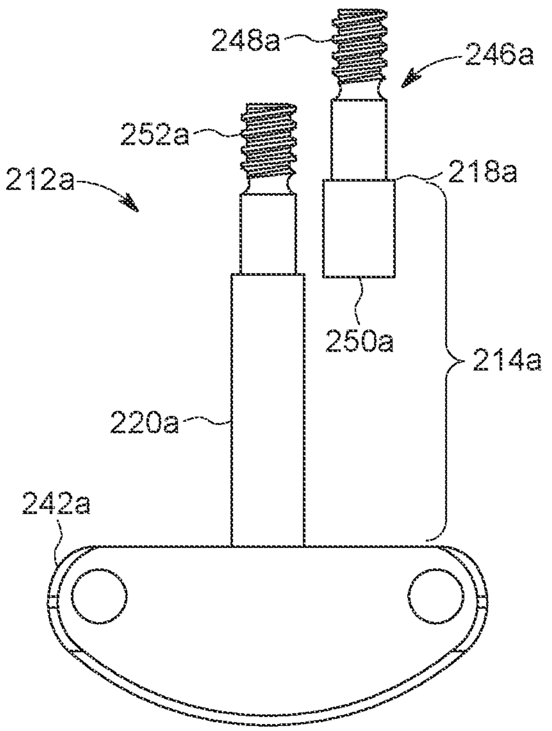
FIGS. 3A-3C are front elevation views of studs usable with the lock of FIG. 1 according to further examples.
Figure 3B:
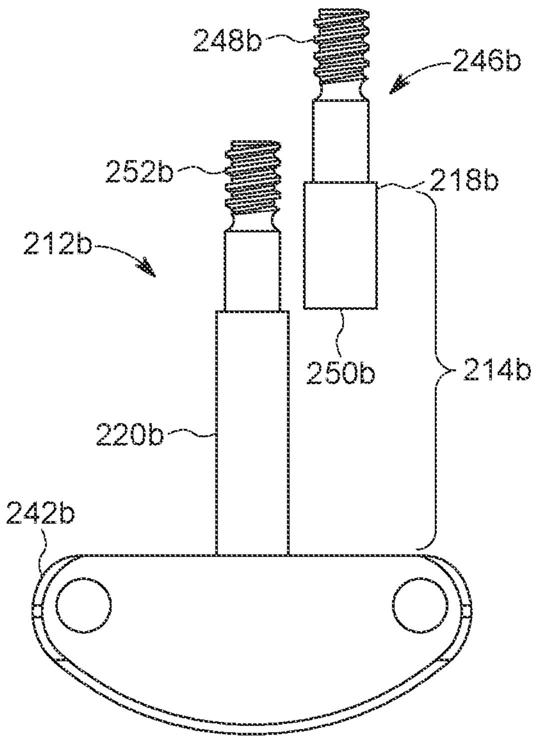
Figure 3C:
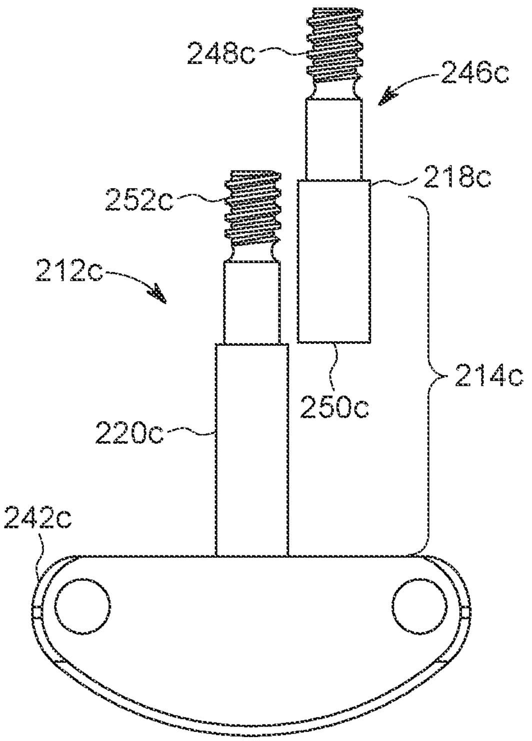

FIGS. 3A-3C illustrate studs 212*a*, 212*b*, 212*c* according to further examples that may be used in lock 10 of FIG. 1. Each stud 212*a*, 212*b*, 212*c* includes a post 220*a*, 220*b*, 220*c* extending proximally from a respective head 242*a*, 242*b*, 242*c* and a removable extension 250*a*, 250*b*, 250*c*, with a ratio of the length of the post to the length of the removable extension differing for each stud. A secondary plug 252*a*, 252*b*, 252*c* that may be received in a recess in a distal end of the respective extension 250*a*, 250*b*, 250*c* extends from a proximal end of each post 220*a*, 220*b*, 220*c*. In the illustrated example, each secondary plug 252*a*, 252*b*, 252*c* is externally threaded and may engage with internal threading within the distal recess of the respective extension 250*a*, 250*b*, 250*c*, but the extensions may be removably joinable to the posts by other structures, such as internal threaded recesses in the posts and secondary plugs extending dismally from the extensions.

Each extension 250*a*, 250*b*, 250*c* includes barrel 218*a*, 218*b*, 218*c* and a primary plug 246*a*, 246*b*, 246*c* extending proximally from the barrel having an externally threaded portion 248*a*, 248*b*, 248*c*. Each barrel 218*a*, 218*b*, 218*c* has a diameter equal to, or, in some examples, less than the diameter of the respective post 220*a*, 220*b*, 220*c*, so a barrel and post can cooperate to provide a shank 214*a*, 214*b*, 214*c* when a secondary plug 252*a*, 252*b*, 252*c* is received in a respective one of the extensions 250*a*, 250*b*, 250*c*. Barrel 218*a* provides equal to or about 21% of a length of shank 214*a*, excluding primary plug 246*a* and secondary plug 252*a*, barrel 218*b* provides equal to or about 28% of a length of shank 214*b*, excluding primary plug 246*b* and secondary plug 252*b*, and barrel 218*c* provides equal to or about 35% of a length of shank 214*c*, excluding primary plug 246*c* and secondary plug 252*c*. Posts 220*a*, 220*b*, 220*c* have a rough or textured surface, or are otherwise engageable by grip 16, while barrels 218*a*, 218*b*, 218*c* have smooth surface, or are otherwise unengageable by the grip, so each shank 214*a*, 214*b*, 214*c* provided by a combination of a post and a barrel will have a proximal, unengageable portion provided by the barrel and a distal, engageable portion provided by the post.

Figure 3D:
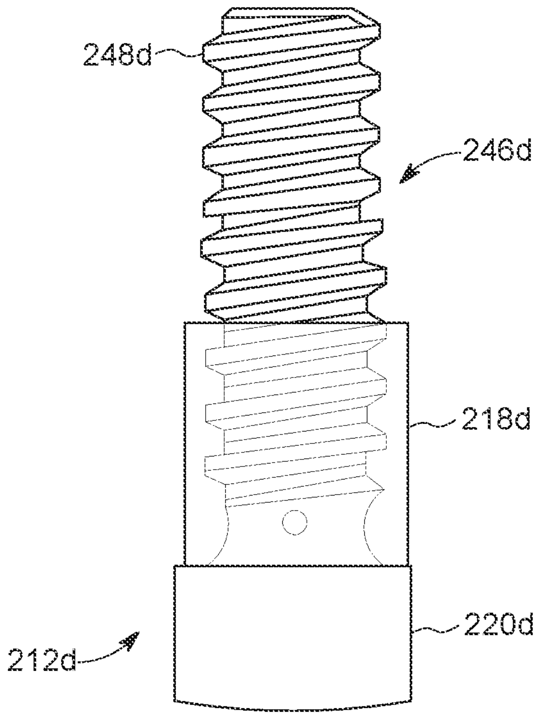
FIG. 3D is a front elevation view of a portion of a stud according to another example.

FIG. 3D illustrates a proximal end of a stud 212*d* according to another example that may be used in lock 10 of FIG. 1. Similar to the foregoing studs 212*a*, 212*b*, 212*c*, stud 212*d* includes an engageable post 220*d*, and a plug 246*d* extends proximally from a proximal end of the post. Post 220*d* may be engageable by inclusion of texture, notches, or any of the features facilitating engage ability described above with regard to any previous example. In the example of FIG. 3D, threaded portion 248*d* is relatively long, such that it can be adequately secured to an actuator rod or other receiving tool when only partially threaded therein. In the illustrated example, threaded portion 248*d* extends along an entire length of plug 246*d*, but in other examples the threaded portion may only be part of the plug. Plug 246*d* may also be longer relative to stud 212*d* overall than any of plugs 246*a*, 246*b*, 246*c*, 252*a*, 252*b*, 252*c* are relative to their respective studs 212*a*, 212*b*, 212*c*.

Stud 212*d* is provided with a hollow barrel 218*d* with an unengageable outer surface, which may be smooth or otherwise unengageable in the manner described above with regard to any of the foregoing examples. An outer surface of barrel 218*d* may also be narrower in diameter than post 220*d*. Barrel 218*d* may be disposed over plug 246*d* such that the barrel and post 220*d* together act as a shank having an engageable and unengageable portion much like those described above with regard to any of the foregoing examples, with the barrel providing the unengageable portion and the post providing the engageable portion. Relative lengths of barrel 218*d* and post 220*d* may be the same as the relative lengths of the engageable and unengageable portions of any of the foregoing examples. Barrel 218*d* or any extension 250*a*, 250*b*, 250*c* may be made of the same material or a different material as the corresponding stud 212*a*, 212*b*, 212*c*, 212*d*. Suitable materials for studs, extensions, or barrels include any sufficiently durable materials known to be usable in medical implants. Certain polymers, ceramics, and metals or metal alloys are among such materials. Examples of suitable metals or metal alloys include, but are not limited to, titanium, nitinol, cobalt chromium, and elgiloy. Extensions or removable barrels may be, optionally, constructed from a harder or otherwise more damage resistant material than their respective stud, smoother than their respective stud, electro-polished, or treated with a friction-reducing coating.

Lock 10 and any of the above described studs having engageable and unengageable portions, or other apparatus operating according to similar principles, may be used in any application wherein selective restriction of translation along an axis of one component relative to another may be needed. Some examples of applications for lock 10 and the studs include any of the valve clips described in U.S. Pat. No. 7,604,646, filed May 16, 2005, or U.S. Pat. No. 8,057,493, filed Dec. 18, 2009, the entireties of which are hereby incorporated herein by reference.

Figure 4A:
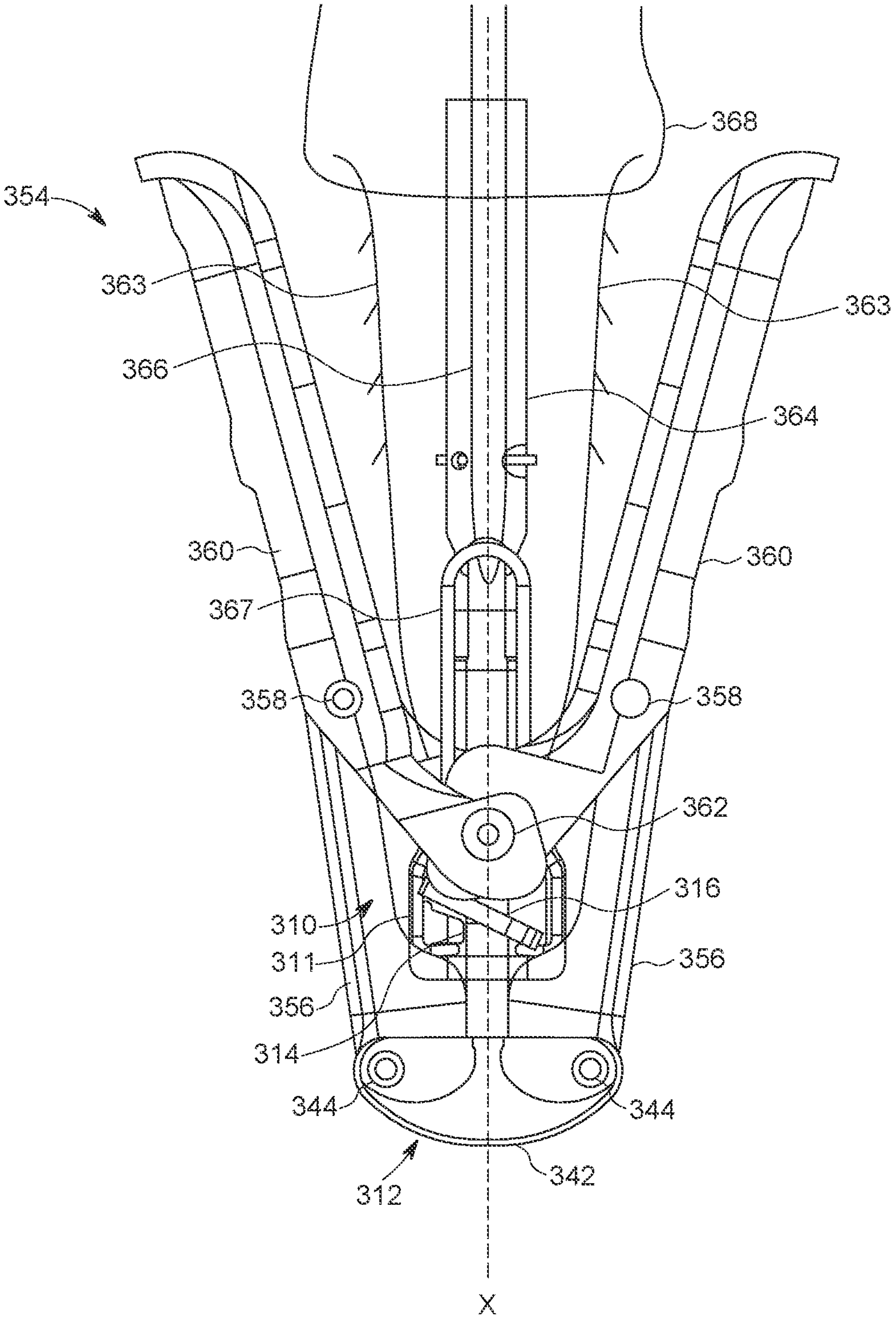
FIGS. 4A-4C are illustrations of a mitral valve clip in different configurations.

Clip 354, illustrated in FIG. 4A, is one example of an application for the lock and studs described above. Clip 354 bears general similarity to some clips described in U.S. Pat. Nos. 7,604,646 and 8,057,493 and may be delivered with similar tools. One application for clip 354 of the illustrated example is treatment of mitral valve regurgitation as detailed below, but similar clips, and the teachings of the present disclosure in general, may also be applied in treating other valves in the heart or throughout the body. Specifically, the teachings of the present disclosure are not limited to the treatment of bicuspid valves and may, for example, be used in substantially the same manner to treat tricuspid valves. Clip 354 includes lock 310 and a stud 312 extending there through along longitudinal axis X. Lock 310 is generally alike to lock 10 of FIG. 1, and stud 312 is generally alike to any stud 12, 112*b*, 112*c*, 112*d*, 212*a*, 212*b*, 212*c*, 812 of FIG. 1, 2B-3C, or 8. Lock 310 thus includes a grip 316 biased into contact with a shank 314 of stud 312. Shank 314 includes both an engageable and an unengageable portion similar to those described above, though a boundary between the two portions is not visible in FIG. 4A.

Figure 4B:
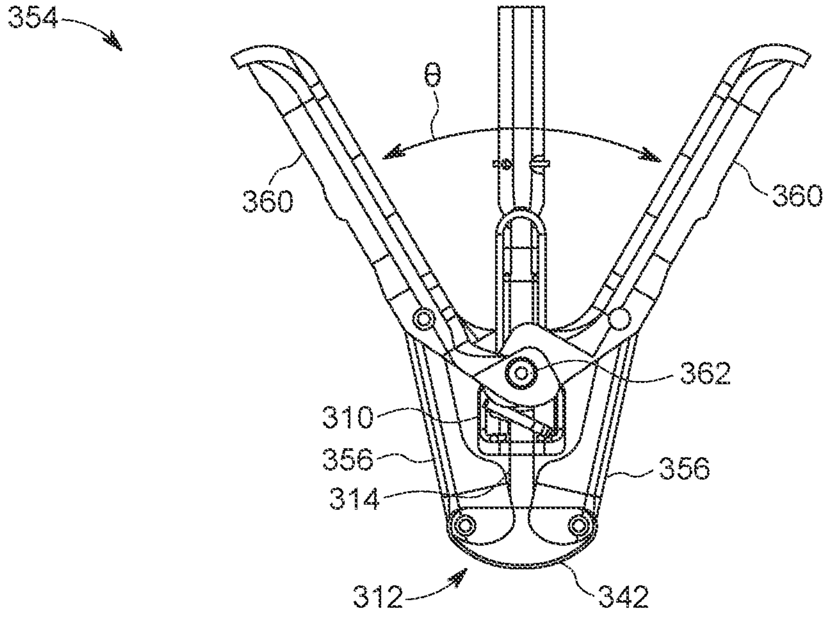
Figure 4C:
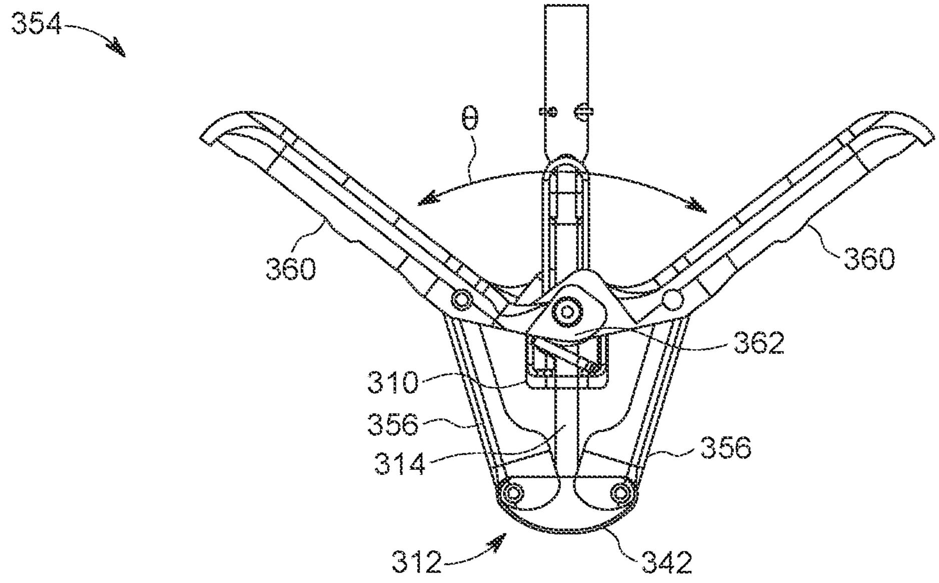

Two bars 356 are coupled to head 342 of stud 312. Each bar 356 is coupled at its distal end, relative to a position of clip 354 illustrated in FIG. 4A, to a hole 344 in head 342 and each of the bars 356 is coupled at its proximal end, again relative to the position of the clip in FIG. 4A, by a primary hinge 358 to a respective arm 360. Each arm 360 is also coupled by a secondary hinge 362, at a location spaced from the respective primary hinge 358 to a frame 311 of lock 310. Proximal or distal travel of stud 312 will cause travel of bars 356 in generally the same direction, causing the bars in turn to pull or push arms 360 to pivot about secondary hinge 362. Head 342, bars 356, arms 360, and frame 311 are therefore respectively coupled such that, as shown in FIGS. 4A-4C, an angle θ between the arms on a proximal side thereof increases as stud 312 travels distally relative to lock 310, and the angle between the arms decreases as the stud travels proximally relative to the lock. Proximal-side angle θ between arms 360 thus depends on, or is a function of, the location of stud 312 relative to lock 310.

As a result of the pivoting interconnection of head 342, bars 356, arms 360, and frame 311, movement of the arms is governed, in part, by the characteristics of shank 314. Proximal-side angle θ between arms 360 may be freely widened and narrowed throughout an angular range corresponding to a range of axial positions of stud 312 wherein the engageable portion of shank 314 is entirely distal of a biting edge of grip 316, but pivoting of the arms relative to one another may become restricted once the arms reach an angular position corresponding to an axial position of the stud wherein the grip may contact the engageable portion of the shank.

If lock 310 is configured such that grip 316 can only restrict distal movement of stud 312, such as described above with regard to lock 10 of FIG. 1, then arms 360 will be able to rotate so as to narrow proximal-side angle θ defined between them when the grip engages the engageable portion of shank 314, but the arms will not be able to rotate so as to widen the proximal-side angle defined between them when the grip engages the engageable portion of the shank. In such an example, arms 360 may be freely manipulated to widen and narrow proximal-side angle θ as long as the angle remains relatively large, but after the angle narrows below a locking threshold determined by the length of the engageable portion of shank 314, the angle may only be narrowed until grip 316 is disengaged from the shank 314. The locking threshold of angle θ depends on the length of the engageable portion of shank 314. The locking threshold may be equal to or about 90°. Alternatively, the locking threshold may be an obtuse angle, such as, for example, equal to or about 120°, equal to or about 115°, equal to or about 110°, equal to or about 105°, equal to or about 100°, or equal to or about 95°. In further alternatives, the locking threshold may be an acute angle, such as, for example, equal to or about 80°, equal to or about 70°, equal to or about 60°, equal to or about 45°, or equal to or about 30°. The locking threshold may also fall within any angular range defined between any two of the foregoing numerical examples, or any angle less than any of the foregoing numerical examples. When used with regard to the location of stud 312 relative to frame 311, the term "locking threshold" may refer to the distal-most location of the stud relative to the frame at which grip 316 may engage the engageable portion of shank 314, and the locking threshold for the stud may correspond to a position of arms 360 that would result in any of the foregoing examples of the locking threshold for angle θ. Though not labeled, a distal-side angle is defined between arms 360 on an opposite side of the arms from proximal-side angle θ, and a locking threshold for the distal-side angle is a value below which grip 316 cannot reach the engageable portion of shank 314.

Figure 4D:
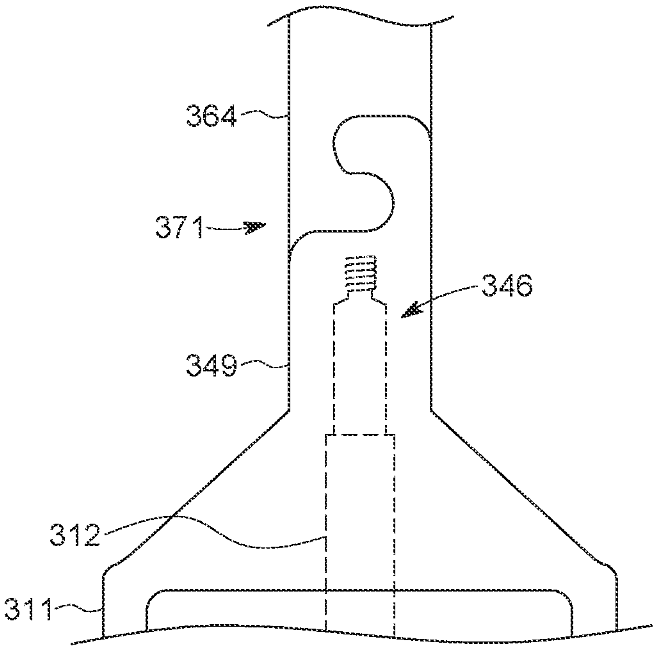
FIG. 4D is a front elevation view of a portion of the clip of FIGS. 4A-4C coupled to a first tool.
Figure 4E:
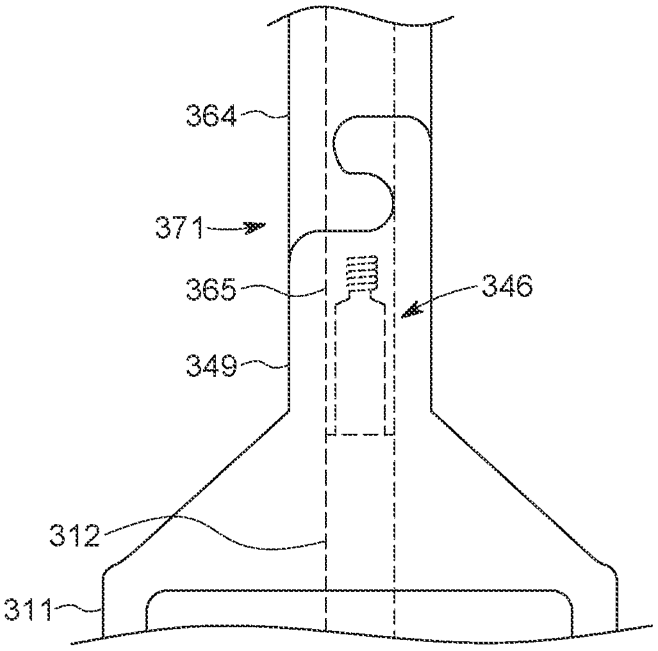
FIG. 4E is a front elevation view of the portion of the clip of FIG. 4D to the first tool and a second tool.

Turning to FIGS. 4D and 4E, with continued reference FIG. 4A, clip 354 is connected at distal ends of tools for controlling the clip. A sheath 364 is releasably connected to a proximal end of frame 311 of lock 310, for example at a proximal sleeve 349 feature similar to proximal sleeve 49 of lock 10 of FIG. 1. The distal end of sheath 364 and the proximal end of proximal sleeve 349 terminate in complementary hooks 371. that prevent axial movement of lock 310 relative to sheath 364 when the complementary hooks are mutually engaged as shown in FIGS. 4D and 4E. As shown in FIG. 4E specifically, an actuator rod 365 may be extended within sheath 364 to engage a proximal end of stud 312. In the illustrated example, a threaded plug 346 defines the proximal end of stud 312 that may be engaged by actuator rod 365 by receipt and threaded engagement of plug 346 by actuator rod 365. However, in other examples, the proximal end of stud 312 may include any kind of feature that may be selectively engaged by a corresponding feature at the distal end of actuator rod 365 to couple the stud to the actuator rod. While actuator rod 365 is engaged to stud 312, the actuator rod may be moved axially, independently of sheath 364, to pull or push the stud along longitudinal axis X. Complementary hooks 371 cannot disengage while actuator rod 365 is engaged with stud 312, and when complementary hooks 371 are engaged, lock 310 cannot move relative to sheath 364. Thus, when complementary hooks 371 are mutually engaged and actuator rod 365 is engaged to stud 312 as shown in FIG. 3E, sheath 364 may be manipulated to move clip 354 as a whole, and actuator rod 365 may be moved within sheath 364 to change angle θ between arms 360. When clip 354 should be released, actuator rod 365 may be disengaged from stud 312, which would be accomplished by rotating the actuator rod within sheath 364 in the illustrated arrangement to unthread the actuator rod from plug 346. When actuator rod 365 is not engaged to stud 312, complementary hooks 371 may slip free of one another by moving away from each other in a direction perpendicular to longitudinal axis X to free clip 354 from sheath 364.

Clip 354 also includes two resiliently flexible tabs, grippers, or anchors 363 connected to the clip near secondary hinge 362. Anchors 363 include barbs facing away from longitudinal axis X and toward arms 360. Each anchor 363 is configured to be elastically self-biased away from longitudinal axis X and toward a respective arm 360. In the arrangement illustrated in FIG. 4A, both anchors 363 are pulled away from their respective arm 360 by tension on an anchor line 368, which may be, for example, a wire, cord, suture, or similar object. Anchor line 368 extends through an eyelet (not visible in FIG. 4A) at a proximal end of each anchor 363, so proximal tension on both ends of the anchor line draws the anchors toward central axis X and away from arms 360. In alternative to the illustrated example, anchor line 368 may instead be two separate lines, each of which may be independently connectable to the actuator rod or sheath 364 and threaded through a respective anchor 363.

The barbs on each anchor 363 can sink into a leaflet in a heart valve, such as a mitral valve. Anchor line 368 may extend out of the heart while clip 354 is disposed within the annulus of the valve such that a physician may manipulate the anchor line to draw in or release anchors 363. For example, the physician may use anchor line 368 to initially draw anchors 363 toward longitudinal axis X, then release the anchors while clip 354 is disposed within the annulus of the valve and arms 360 are open to trap each leaflet of the valve between a respective anchor and arm. One end of anchor line 368 may be pulled until the entire anchor line exits the patient.

Clip 354 further includes a harness 367 providing for selective release of grip 316. In the illustrated example, harness 367 is resiliently flexible and generally U-shaped. Though partially obscured in FIG. 4A, a first end of harness 367 is a hook, such as first hook 36 depicted in FIG. 1, which is positioned so as to be movable to pull grip 316 away from shank 314. A second end of harness 367 is fixed to clip 354, similar to second hook 38 depicted in FIG. 1. Proximal tension on harness 367 will therefore draw the first end of the harness proximally so as to counteract bias upon grip 316 and pull the grip away from shank 314, putting lock 310 into an actively or manually disengaged state. When the proximal tension on harness 367 is released, the harness will return to its rest shape wherein the harness does not prevent grip 316 from contacting shank 314.

Harness line 366, which may be, for example, a wire, cord, suture, or similar object, is looped through harness 367 such that proximal tension on both ends of the harness line will cause the harness to bend and pull grip 316 away from shank 314. Harness line 366 may extend out of the heart when clip 354 is disposed within the annulus of a valve of the heart such that a physician may manipulate the harness line to cause harness 367 to selectively allow or prohibit contact between grip 316 and shank 314. For example, clip 354 may be delivered into the heart in a configuration wherein angle θ is as small as possible, such as 0°, or otherwise small enough that grip 316 engages the engageable portion of shank 314. The physician may then pull on harness line 366 to cause harness 367 to disengage grip 316 from shank 314 so that arms 360 may spread apart. The physician may pull harness line 366 as many times as necessary manually disengage lock 10 and spread arms 360 after angle θ falls below the locking threshold wherein grip 316 may engage the engageable portion of shank 314.

Harness 367 as illustrated is only one example of a structure enabling selective movement of grip 316. For example, instead of harness 367, harness line 366 may be looped through or around any element connected to clip 354 so as to be biased away from grip 316 but movable to pull the grip away from shank 314 when tension is applied to the harness line.

Though not illustrated, clip 354 may be covered in a material conducive to tissue growth or otherwise conducive to successful and permanent securement of clip 354 to two leaflets of a heart valve. The covering material may be, for example, a porous or weblike structure, and may be constructed of any biocompatible material, such as certain polymers, and may include drugs or medication.

Figure 5:
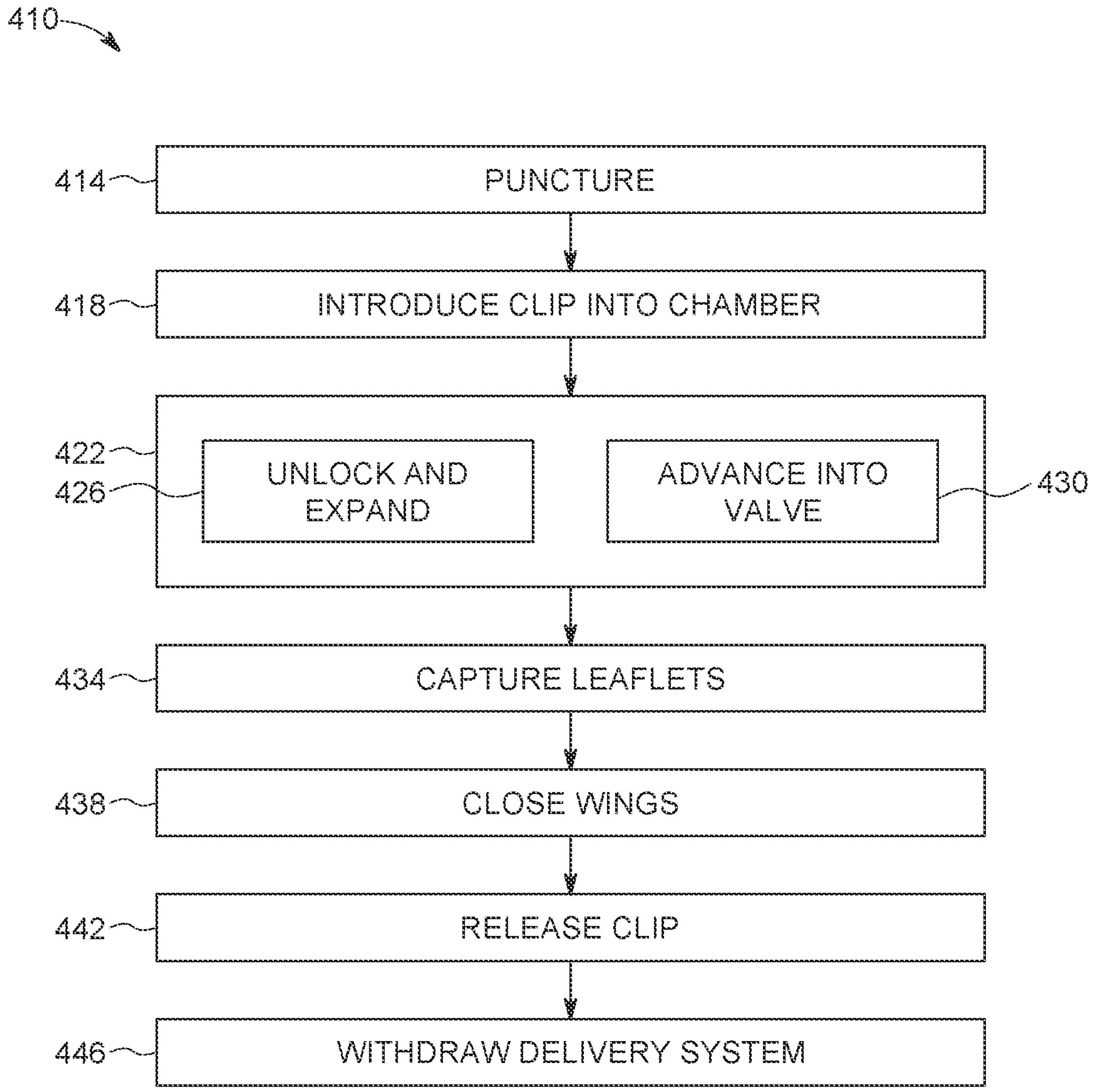
FIG. 5 illustrates a process of implanting the clip of FIGS. 4A-4C.

FIG. 5 illustrates a process 410 for delivering clip 354 into a heart valve, such as a mitral valve. In a puncturing step 414, part of the heart may be punctured to allow introduction of clip 354. For example, a guidewire and/or needle may be introduced into the patient, such as through the jugular vein, femoral vein, or femoral artery, and guided so as to puncture a wall of the left atrium, such as the septum, to allow an introducing catheter for clip 354 to enter the left atrium. Dilators may be advanced over the puncturing wire to expand the hole before the catheter is advanced into the left atrium.

In an introducing step 418, clip 354 is introduced into the left atrium through the catheter. So that the catheter may be relatively narrow, thus minimizing the hole into the left atrium, clip 354 may be introduced into the left atrium in a configuration wherein proximal-side angle θ between arms 360 has a smallest possible value, such as 0°.

Within a placing stage 422, an unlocking step 426 and an advancing step 430 may be performed in any order. In expanding step 426, the physician manually disengages grip 316 from the engageable portion of shank 314, such as by applying tension to harness line 366, and widens angle θ, such as by using the actuator rod within sheath 364 to push stud 312 distally relative to lock 310, while holding the grip out of contact with the shank. Angle θ may be widened above the locking threshold below which grip 316 may contact the engageable portion of shank 314. In such instance, the physician may cease applying force to harness line 366 to release grip 316 into contact with the unengageable portion of shank 314 or the actuator rod and continue to narrow or widen angle θ without further manipulation of the grip until the angle falls below the locking threshold. By releasing grip 316 into contact with the unengageable portion of shank 314 or the actuator rod, the physician permits lock 310 to enter a passively disengaged state. In advancing step 430, clip 354 is advanced into the annulus of the mitral valve to a position wherein the mitral valve leaflets may be captured between anchors 363 and arms 360.

Each mitral valve leaflet is captured between a respective anchor 363 and arm 360 in a capturing step 434. Anchors 363 may be pulled toward longitudinal axis X between expanding step 426 and capturing step 434, such as by applying tension to anchor line 368, or may be held close to longitudinal axis X throughout the expanding step and until the capturing step. An exact position for clip 354, arms 360, and anchors 363 wherein the valve leaflets may be captured will vary depending on individual patient anatomy and the timing of the capture relative to the beat of the heart. For that reason, the physician may need to make multiple attempts to capture the leaflets during capturing step 434. Capturing step 434 may therefore include repeated adjustment of angle θ, adjustment of the position of clip 354, and pulling of anchors 363 away from arms 360. Because leaflet capture will tend to be easiest to accomplish when angle θ is relatively large, the physician may be able to widen and narrow the angle between arms 360 repeatedly throughout capturing step 434 while allowing grip 316 to remain in contact with the actuator rod and/or unengageable portion of shank 314. However, if angle θ falls below the locking threshold before the leaflets are satisfactorily captured, and the physician wishes to widen the angle again, the physician may disengage grip 316 from the engageable portion of shank 314, such as by pulling on harness line 366.

After some capture attempts, the physician may assess the security of the leaflets between their respective anchor 363 and arm 360. Capturing step 434 concludes when each leaflet is satisfactorily secured between a respective anchor 363 and arm 360. Harness line 366 and anchor line 368 may be withdrawn from the patient at any time after capturing step 434.

After capturing step 434, the physician may narrow angle θ in a closing step 438 while the leaflets remain trapped between anchors 363 and arms 360. During closing step 438, angle θ may be narrowed to 0°, to the smallest value of the angle made possible by the structure of clip 354, or to any value of the angle θ that the physician finds satisfactory and at which grip 316 may engage the engageable portion of shank 314. In examples wherein grip 316 is biased to contact shank 314 whenever the physician does not apply tension to harness line 366, the grip engages the engageable portion of shank 314 at the end of closing step 438 so arms 360 will not move relative to one another and angle θ will remain constant at a final locked angle after the closing step unless the physician purposefully interferes. As such, if the physician has permitted lock 310 to enter the passively disengaged state prior to closing step 438, and the physician does not manually disengage the lock during the closing step, the lock will automatically transition to the engaged state when angle θ falls below the locking threshold during the closing step. In this instance, "automatic" refers to the self-acting or self-regulating nature of the apparatus in the transition from one state to another, meaning components of the apparatus itself cause the apparatus to transition between states when an independent circumstance occurs such as by mechanical action. In this specific example, lock 310 automatically transitions from the passively disengaged state to the engaged state when the independent circumstance of stud 312 moving past the locking threshold occurs because, upon such occurrence, mechanical interaction of lock components including frame 311, grip 316, and a spring or similar biasing element will cause the grip to bite into the engageable portion of shank 314. However, "automatic" here does not refer only to mechanical action.

The physician may therefore disengage grip 416 from the engageable portion of shank 314 one during expanding step 426, then refrain from interfering with grip 416 throughout the rest of delivery process 410 unless angle θ drops again below the locking threshold before capturing step 434 is completed.

Because lock 310 automatically transitions from the passively disengaged state to the engaged state when angle θ drops below the locking threshold, and because angle θ may be narrowed while the locking mechanism is in the engaged state, the physician may not need any tool for manually transitioning the locking mechanism 310 into or out of the engaged state, or between any two states, to remain in the patient after capturing step 434 is completed. The physician may therefore remove harness line 366 after capturing step 434 and before closing step 438 if desired. Such early removal of harness line 366 is particularly viable if the physician intends to leave clip 354 implanted in the heart with angle θ at the smallest possible value.

After closing step 438, clip 354 is released in releasing step 442. In releasing step 442, the actuator rod is disengaged from shank 314, such as by rotating the actuator rod to unthread the actuator rod from a plug extending from a proximal end of the shank, and sheath 364 is disengaged from clip 354, such as by moving the sheath so as to free a hook at the distal end of the sheath from a complementary hook at a proximal end of frame 311. Sheath 364 and any other tools used for delivery of clip 354 that remain within the patient after releasing step 442, which may include the catheter, actuator rod, harness line 366, and anchor line 368, are removed from the patient in a withdrawal step 446.

Figure 6:
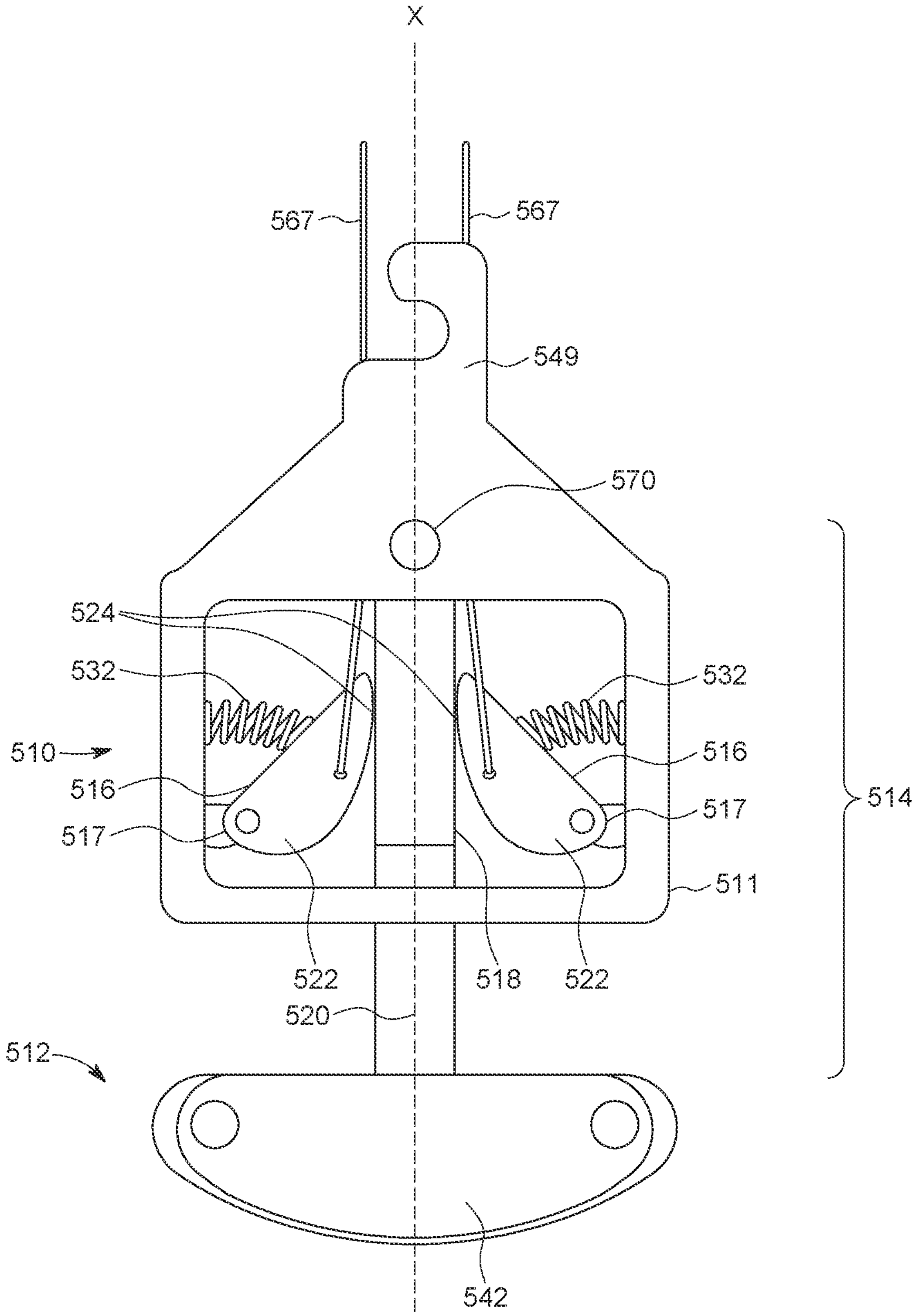
FIG. 6 is a front elevation view of a lock and stud according to another arrangement.

FIG. 6 illustrates a lock 510 according to another arrangement. Lock 510 of FIG. 6 operates according to similar principles as lock 10 of FIG. 1 and is therefore compatible with any of the above described studs, clips, or delivery processes. Stud 512 extends through lock 510 along longitudinal axis X. Stud 512 includes a shank 514 extending from a head 542, and the shank includes unengageable portion 518 further from the head and engageable portion 520 nearer the head. Lock 510 includes frame 511. Frame 511 includes proximal sleeve 549 which extends proximally and ends in a hook for engaging a complementary hook of a delivery tool, such as sheath 364. Frame 511 also includes a hole 570 which may serve as part of a hinge wherein arms of a clip may connect to the frame, similar to secondary hinge 362.

Lock 510 includes two grips 516, each on an opposite side of longitudinal axis X. Each grip 516 is connected to frame 511 by a respective hinge 517. Each grip 516 has a contacting side 522 including a contact point 524 where the grip contacts shank 520. Each grip 516 is biased by a respective spring 532 disposed between the grip and frame 511. Each spring 532 biases the respective grip 516 with a force moment encouraging arcuate travel of the grip's contact point 532 about the respective hinge 517. Each spring 532 and contact point 524 is located proximally of the hinge 517 connecting the respective grip 516 to frame 511. As such, in the configuration of lock 510 illustrated in FIG. 6, with stud 512 extending through the lock along longitudinal axis X, each contact point 524 is biased distally and toward axis X. For that reason, when contact points 524 are frictionally engaged to engageable portion 520 of shank 514, proximal force on stud 512 will create a moment on each grip 516 about the respective hinge 517 opposite the moment created by the respective spring 532, thus pushing both contact points 524 away from longitudinal axis X. Similar to lock 10 of FIG. 1, lock 510 is therefore a one-way lock that restricts distal travel of stud 512 when the stud is located proximally enough for contact points 524 to contact engageable portion 520, but permits proximal travel of the stud until head 542 abuts frame 511 or some external obstacle prevents further travel of the stud. Grips 516 may be manually disengaged to permit distal travel of stud 512 after contact points 524 have engaged engageable portion 520 of shank 514 by applying proximal tension to harness 567, each of which is connected to one of the grips at a location remote from the respective hinge 517.

Figure 7:
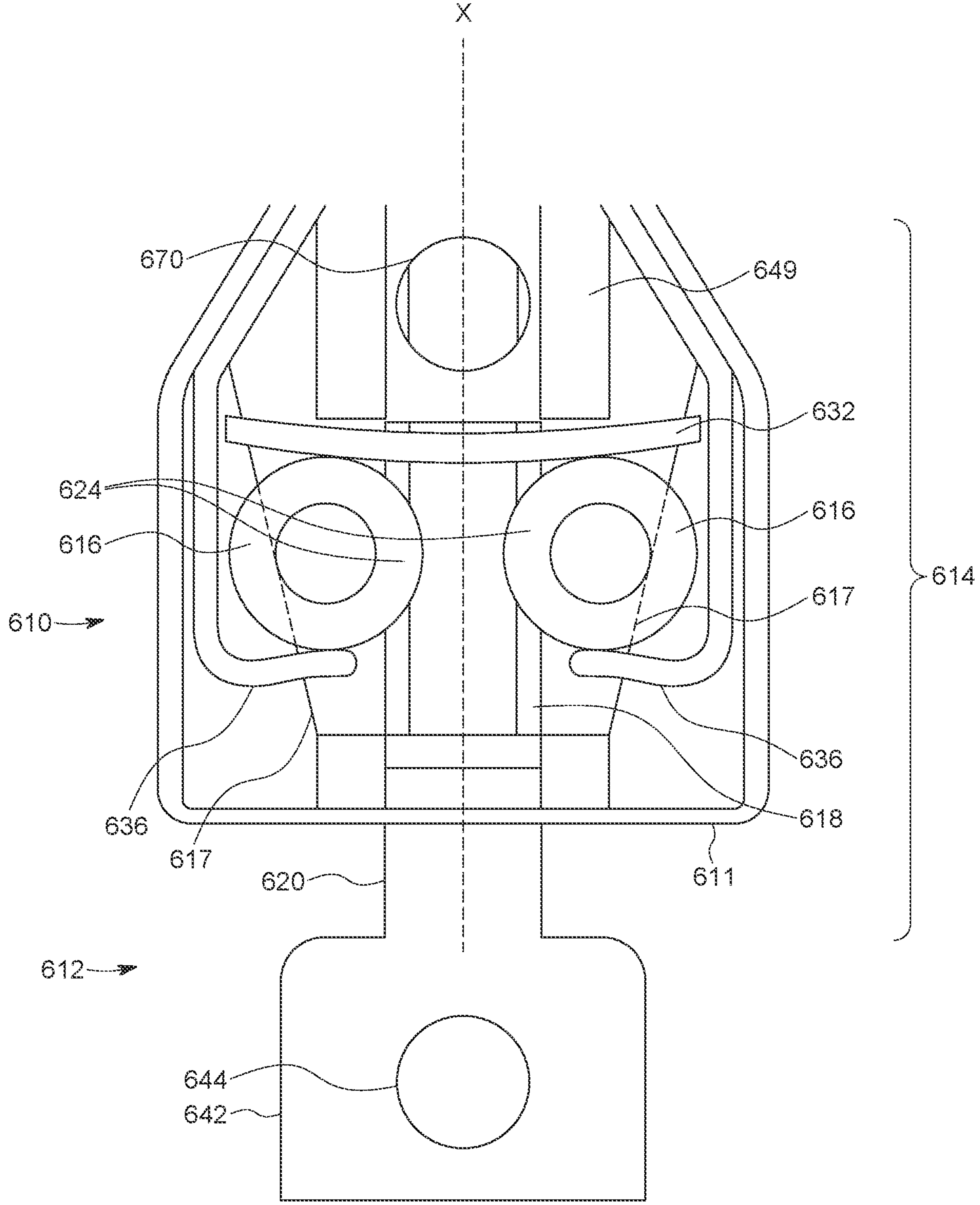
FIG. 7 is a front elevation view of a lock and stud according to yet another arrangement.

FIG. 7 illustrates a lock 610 according to another arrangement. Lock 610 of FIG. 7 operates according to similar principles as lock 10 of FIG. 1 and is therefore compatible with studs, clips, or delivery processes similar to any of those described above. Stud 612 extends through lock 610 along longitudinal axis X. Stud 612 includes a shank 614 extending from a head 642, and the shank includes unengageable portion 618 further from the head and engageable portion 620 nearer the head. Lock 610 includes frame 611. Frame 611 includes proximal sleeve 649 which extends proximally and may end, for example, in a hook for engaging a complementary hook of a delivery tool, such as sheath 364. Frame 611 also includes a hole 670 which may serve as part of a hinge wherein arms of a clip may connect to the frame, similar to secondary hinge 362.

Lock 610 includes two grips 616, each on an opposite side of longitudinal axis X. Each grip 616 is disposed within frame 611 so as to travel along a respective track 617. Each track 617 is sloped to be relatively far from longitudinal axis X at a proximal end of the track and relatively near to the longitudinal axis at the distal end of track. Thus, as grips 616 travel distally along their respective tracks 617, the grips will become nearer to shank 614 or engage the shank with greater lateral force. Both grips 616 are biased distally. In the illustrated example, each grip 616 is biased by a respective end of a leaf spring 632 with a functional fulcrum located between the grips. The distal bias on grips 616 has an inward component because of tracks 617. Similarly, when contact points 624 are frictionally engaged to engageable portion 620 of shank 614, proximal force on stud 612 will push grips 616 both proximally and away from longitudinal axis X along tracks 617, thus pushing both contact points 624 away from the shank. Similar to lock 10 of FIG. 1, lock 610 is therefore a one-way lock that restricts distal travel of stud 612 when the stud is located proximally enough for contact points 624 to contact engageable portion 620, but permits proximal travel of the stud until head 642 abuts frame 611 or some external obstacle prevents further travel of the stud. Grips 616 may be manually disengaged to permit distal travel of stud 612 after contact points 624 have engaged engageable portion 620 of shank 614 by applying proximal tension to hooks 636, each of which extends across part of a distal side of a respective grip. Hooks 636 may each individually be connected to a line, or may both be connected by a wire forming a harness around which a line may be looped.

In the example illustrated in FIG. 6, stud 612 has a relatively narrow head 642 that includes only one through-hole 644. However, lock 610 is compatible with any of the wide-head studs 12, 112*a*, 112*b*, 112*c*, 112*d*, 212*a*, 212*b*, 212*c*, 312, 512, 812, or variations thereon described above. Moreover, stud 612 is generally similar to the other studs of the present disclosure except for the width and number of holes in head 642, and is therefore compatible at least with locks 10, 510. Stud 612 may also be incorporated into a clip similar to clip 354, except that a clip including stud 612 of FIG. 6 would have bars, otherwise similar to bars 356, configured to both be coupled to the shame hole 644 at their proximal ends.

Figure 9:
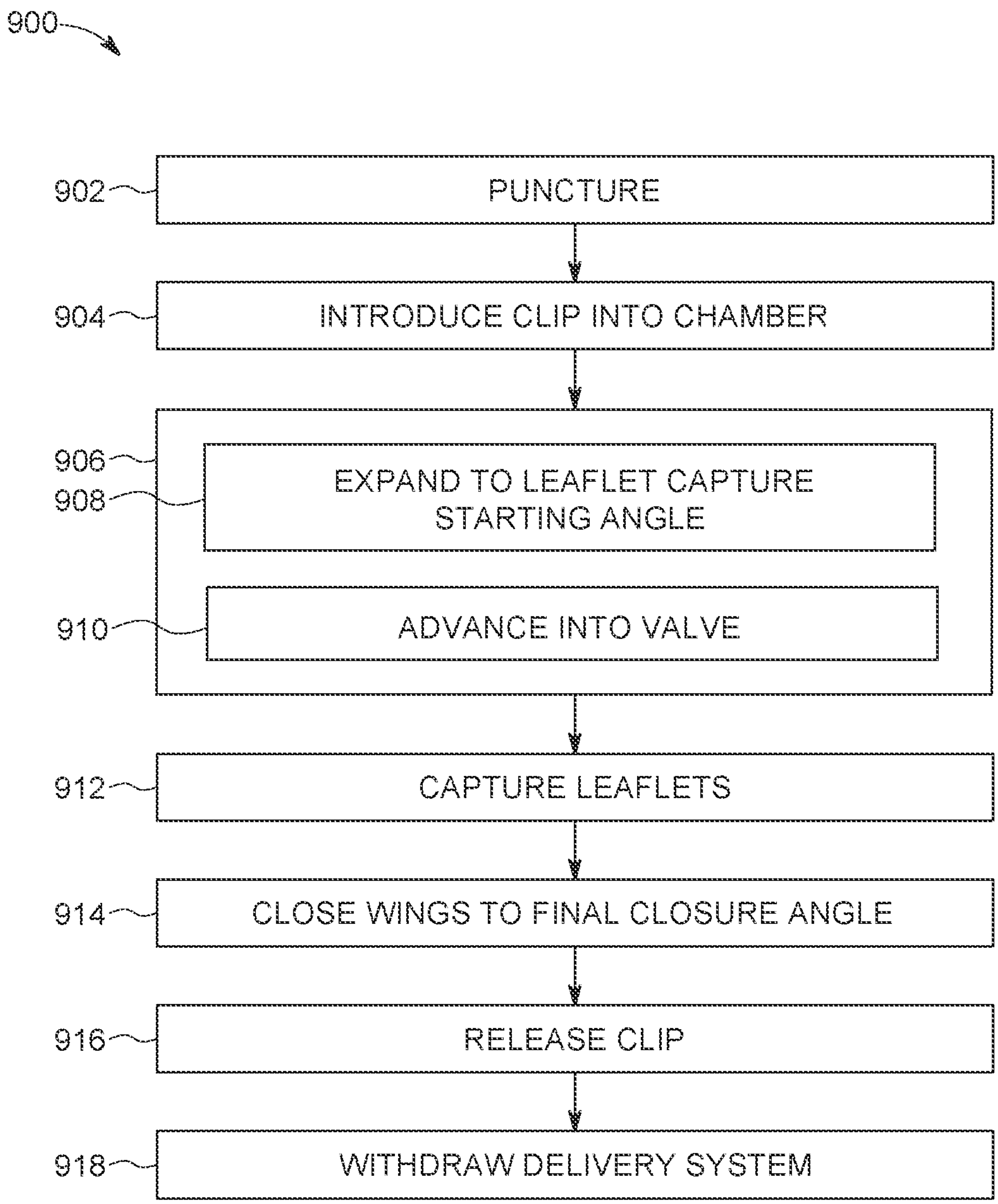
FIG. 9 illustrates a process of implanting the clip of FIGS. 4A-4C.

FIG. 9 illustrates a process 900 for delivering the clip 354 into a heart valve, such as a mitral valve. In a puncturing step 902, part of the heart may be punctured to allow introduction of the clip 354. For example, a guidewire and/or needle may be introduced into the patient, such as through the jugular vein, femoral vein, or femoral artery, and guided so as to puncture a wall of the left atrium, such as the atrial septum, to allow an introducing catheter for the clip 354 to enter the left atrium. Dilators may be advanced over the puncturing wire to expand the hole before the catheter is advanced into the left atrium.

In an introducing step 904, the clip 354 is introduced into the left atrium through the catheter. The clip 354 may be introduced into the left atrium in a configuration where the proximal-side angle θ between the arms 360 has a smallest possible value, such as but not limited to 0°. The proximal-side angle θ may be selected such that a diameter of the catheter is minimized, thus minimizing a size of the hole in the atrial septum.

A placing stage 906 includes an expanding step 908 and an advancing step 910, which may be performed in any order. In the expanding step 908, the physician manually disengages the grip 316 from the engageable portion of the shank 314, such as by applying tension to the harness line 366, and widens angle θ, while holding the grip 316 out of contact with the shank 314. The angle θ may be widened to a leaflet capture starting angle above the locking threshold below which the grip 316 may contact the engageable portion of the shank 314. In some examples, the leaflet capture starting angle is about 90 degrees. One of the potential benefits of the leaflet capture starting angle being about 90 degrees is that, under visualization, an angle of 90 degrees may be easily discerned. In other words, many, most, or all users of clip 354 would find a right angle to be a relatively easily discernable configuration during imaging, compared to other angles that are between 0 degrees and 90 degrees, or between 90 degrees and 180 degrees. By releasing the grip 316, the grip 316 contacts the unengageable portion of shank 314 or the actuator rod at the leaflet capture starting angle, permitting the lock 310 to enter a passively disengaged state before the capturing step 912. The anchors 363 may be pulled toward the longitudinal axis X between the expanding step 908 and the capturing step 912, such as by applying tension to the anchor line 368, or may be held close to the longitudinal axis X throughout the expanding step 908 and until the capturing step 912. In the advancing step 910, the clip 354 is advanced into the annulus of the mitral valve to a position wherein the mitral valve leaflets may be captured between the anchors 363 and the arms 360. In examples, the clip 354 is positioned above a mitral regurgitation jet such that the longitudinal axis X is perpendicular to the mitral valve.

In the capturing step 912, each mitral valve leaflet is captured between a respective anchor 363 and arm 360. The physician may continue to narrow or widen angle θ from the leaflet capture starting angle without further manipulation of the grip 316 until the angle falls below the locking threshold. An exact position for the clip 354, arms 360, and anchors 363 wherein the valve leaflets may be captured will vary depending on individual patient anatomy and the timing of the capture relative to the beat of the heart. For that reason, the physician may need to make multiple attempts to capture the leaflets during the capturing step 912. The capturing step 912 may therefore include repeated adjustment of angle θ, adjustment of the position of the clip 354, and pulling of the anchors 363 away from the arms 360. Because leaflet capture will tend to be easiest to accomplish when angle θ is larger, the physician may be able to widen and narrow the angle between arms 360 repeatedly throughout the capturing step 912 while allowing the grip 316 to remain in contact with the actuator rod and/or unengageable portion of the shank 314. However, if angle θ falls below the locking threshold before the leaflets are satisfactorily captured, and the physician wishes to widen the angle again, the physician may disengage the grip 316 from the engageable portion of the shank 314, such as by pulling on the harness line 366. The physician may assess the security of the leaflets between their respective anchor 363 and arm 360. Capturing step 912 concludes when each leaflet is satisfactorily secured between a respective anchor 363 and arm 360. The harness line 366 and the anchor line 368 may be withdrawn from the patient at any time after capturing step 912.

After the capturing step 912, the physician may narrow angle θ in a closing step 914 while the leaflets remain trapped between the anchors 363 and the arms 360. During the closing step 914, angle θ may be narrowed to a final closure angle. The final closure angle may be an angle θ that the physician finds satisfactory and at which the grip 316 may engage the engageable portion of the shank 314. The final closure angle may approach 0 degrees, to the smallest value of the angle made possible by the structure of the clip 354. In examples, the final closure angle is between about 10 degrees to about 30 degrees.

In examples wherein the grip 316 is biased to contact the shank 314 whenever the physician does not apply tension to the harness line 366, the grip 316 engages the engageable portion of the shank 314 at the end of closing step 914 so the arms 360 will not move relative to one another and angle θ will remain constant at a final locked angle after the closing step unless the physician purposefully interferes. As such, if the physician has permitted the lock 310 to enter the passively disengaged state prior to closing step 914, and the physician does not manually disengage the lock during the closing step, the lock will automatically transition to the engaged state when angle θ falls below the locking threshold during the closing step. In this instance, "automatic" refers to the self-acting or self-regulating nature of the apparatus in the transition from one state to another, meaning components of the apparatus itself cause the apparatus to transition between states when an independent circumstance occurs such as by mechanical action. In this specific example, the lock 310 automatically transitions from the passively disengaged state to the engaged state when the independent circumstance of the stud 312 moving past the locking threshold occurs because, upon such occurrence, mechanical interaction of lock components including the frame 311, the grip 316, and a spring or similar biasing element will cause the grip to bite into the engageable portion of the shank 314. However, "automatic" here does not refer only to mechanical action.

After closing step 914, the clip 354 is released in releasing step 916. In releasing step 916, the actuator rod is disengaged from the shank 314, such as by rotating the actuator rod to unthread the actuator rod from a plug extending from a proximal end of the shank, and the sheath 364 is disengaged from the clip 354. The sheath 364 and any other tools used for delivery of the clip 354 that remain within the patient after releasing step 916, which may include the catheter, actuator rod, harness line 366, and anchor line 368, are removed from the patient in a withdrawal step 918.

To summarize the foregoing, disclosed is a mitral valve clip which may include a stud, a lock, and two arms. The stud may include a shank. The lock may include a frame relative to which the stud is translatable and into which the shank extends. The lock may be able to prevent movement of the stud relative to the lock along an axis in at least one direction by locking engagement of the shank. Two arms may be connected to the lock and the stud such that an angle between the arms depends on a location of the stud relative to the lock. The locking engagement of the shank that prevents movement of the stud relative to the lock in the at least one direction may only be possible when the angle between the arms is equal to or below 95° or about 95°.

Further, in combination with any of the foregoing examples, the lock may prevent movement of the stud relative to the lock in only one direction.

Further, in combination with any of the foregoing examples, the arms may be connected to the lock and the stud such that the angle between the arms will widen as the stud travels in a widening direction relative to the lock, and the locking engagement of the shank may prevent movement of the stud relative to the lock only in the widening direction.

Further, in combination with any of the foregoing examples, the lock may include a grip biased toward contact with the shank by resilient bias, and the locking engagement of the shank is contact between the grip and an engageable portion of the shank under the resilient bias.

Further, in combination with any of the foregoing examples, the shank may include an unengageable portion wherein contact between the grip and the unengageable portion under the biasing force does not prevent movement of the stud in any direction.

Further, in combination with any of the foregoing examples, the engageable portion may have a rougher surface texture than the unengageable portion.

Further, in combination with any of the foregoing examples, the unengageable portion may extends from the engageable portion to an end of the shank.

Further, in combination with any of the foregoing examples, Further, in combination with any of the foregoing examples, the angle between the arms may be a proximal-side angle. A distal-side angle may be defined between the arms on an opposite side of the arms from the proximal-side angle. A threshold value may exist for the distal-side angle below which the locking engagement of the shank that prevents movement of the stud relative to the lock in at least one direction is impossible.

Further, in combination with any of the foregoing examples, the locking engagement of the shank that prevents movement of the stud relative to the lock in the at least one direction may only be possible when the angle between the arms is equal to or below an angle that is any one of 90°, 80°, 70°, 60°, 45°, and 30°.

Further, in combination with any of the foregoing examples, the lock may be configured to automatically engage the shank when the angle between the arms is less than the angle below which engagement of the shank is possible.

Further, in combination with any of the foregoing examples, the lock may be selectively transitionable to a state wherein locking engagement of the shank is impossible regardless of the angle between the arms.

Also disclosed is an assembly comprising a stud, which includes a shank, and a lock. The stud may include a shank. The shank may have a rough-textured portion and a smooth portion aligned radially about a longitudinal axis of the shank with the rough-textured portion. The lock may comprise a frame and a grip. The shank may extend into the frame along the longitudinal axis. The grip may be biased relative to the frame toward the longitudinal axis such that movement of the stud relative to the grip in at least one direction is prevented when the grip contacts the rough-textured portion of the shank, but movement of the stud relative to the grip may not be prevented by the grip when the grip contacts only the smooth portion of the shank.

Further, in combination with any of the foregoing examples, the smooth portion may extend from the rough-textured portion to a terminal end of the shank.

Further, in combination with any of the foregoing examples, the smooth portion and the rough-textured portion may each have a respective diameter centered on the longitudinal axis, and the diameter of the smooth portion may be smaller than the diameter of the rough-textured portion.

Further, in combination with any of the foregoing examples, the terminal end of the shank may be a proximal end of the shank.

Further, in combination with any of the foregoing examples, the shank may extend along a longitudinal axis, and a border between the smooth portion and the rough-textured portion does not lie on a plane normal to the longitudinal axis.

Further, in combination with any of the foregoing examples, the smooth portion may be detachably connected to the rough-textured portion.

Further, in combination with any of the foregoing examples, wherein the grip may be biased relative to the frame toward contact with the longitudinal axis by a bias force that creates a moment on the grip or includes an axial component.

Also disclosed is a mitral valve clip that may comprise the lock or assembly of any one of the foregoing examples and two arms connected to the lock and the stud such that an angle between the arms depends on an axial position of the stud relative to the lock.

Also disclosed is a mitral valve treatment system that may include a clip according to any of the foregoing examples. The system may further include a sheath and an actuator rod. The sheath may have a distal end removably connectable to the frame. The actuator rod may be removably connectable to a proximal end of the shank, extending within the sheath, and longitudinally movable within the sheath.

Further, in combination with any of the foregoing examples, the shank may include a removable extension that includes the proximal end and smooth portion of the shank.

Also disclosed is a method of implanting the mitral valve clip of any of the foregoing examples. The method may include introducing the mitral valve clip into a left atrium of a heart, the clip including two arms rotatable relative to one another and a lock that prevents widening of an angle between the arms when the lock is in an engaged state, and wherein the lock automatically transitions to the engaged state if the angle falls below a locking threshold while the lock is in a passively disengaged state. The method may also include manually disengaging the lock by applying force to a line extending out of the heart. The method may also include expanding the angle between the arms while the lock is manually disengaged. The method may also include permitting the lock to enter the passively disengaged state by releasing the force on the line after the expanding step. The method may also include capturing leaflets of the mitral valve by manipulating anchors of the clip and the arms to trap the leaflets of against the arms while the lock remains in the passively disengaged state, which may include either or both of narrowing and widening an angle between the arms. The method may also include closing the clip by narrowing the angle below the locking threshold while the leaflets are trapped against the arms by the anchors and the lock remains and without manually disengaging the lock.

Further, in combination with any of the foregoing examples, the method may include removing a line used to manually disengage the lock from the heart after the capturing step such that no tool for manually transitioning the lock to or from the engaged state remains in the heart after the capturing step and before the closing step.

Further, in combination with any of the foregoing examples, the locking mechanism may not be manually transitioned to or from the engaged state after the step of permitting the lock to enter the passively disengaged state. Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method for implanting a mitral valve clip comprising:

introducing the mitral valve clip into a left atrium of a heart using a delivery system, the clip including two arms at an angle relative to one another and a lock that prevents widening of the angle when the angle is below a locking threshold value, wherein the lock is in a passively disengaged state when the angle is above the locking threshold value;

manually disengaging the lock and expanding the angle to a leaflet capture starting angle while the lock is manually disengaged;

returning the lock to the passively disengaged state after the angle is expanded to the leaflet capture starting angle;

capturing leaflets of a mitral valve by manipulating the clip to trap the leaflets while the lock remains in the passively disengaged state, and closing the clip to a final closure angle by narrowing the angle while the leaflets are trapped against the arms, wherein the lock transitions from the passively disengaged state to an engaged state without manually disengaging the lock when the angle falls below the locking threshold value.

2. The method of claim 1, wherein the leaflet capture starting angle is about 90 degrees.

3. The method of claim 1, wherein the locking threshold value is about 60 degrees.

4. The method of claim 1, wherein the locking threshold value is about 45 degrees.

5. The method of claim 1, wherein the locking threshold value is between about 30 degrees to about 60 degrees.

6. The method of claim 1, wherein the step of manually disengaging the lock is performed by applying tension to a harness line of the delivery system that extends to the lock.

7. The method of claim 6, wherein the step of returning the lock to the passively disengaged state is performed by releasing the tension on the harness line.

8. The method of claim 1, wherein the clip is introduced into the left atrium with the angle at a smallest possible value.

9. The method of claim 1, further comprising puncturing a hole in a wall of the left atrium, wherein the clip is introduced through the hole.

10. The method of claim 1, wherein the step of manipulating the clip to trap the leaflets includes manipulating anchors of the clip to trap each leaflet against a respective anchor and a respective arm.

11. The method of claim 10, wherein the step of manipulating the anchors of the clips includes applying tension to one or more anchor lines of the delivery system.

12. The method of claim 1, wherein the final closure angle is between about 10 degrees and about 30 degrees.

13. The method of claim 1, further comprising:

releasing the clip from the delivery system; and withdrawing the delivery system.

14. The method of claim 13, wherein the lock remains in the engaged state with the angle remaining at the final closure angle after the clip is released from the delivery system.

15. The method of claim 1, further comprising making a second attempt to capture the leaflets, wherein the step of making the second attempt includes the step of manually disengaging the lock and expanding the angle between the arms up to the leaflet capture starting angle while the lock is manually disengaged.

16. A method for implanting a valve repair clip, the method comprising:

introducing the valve repair clip into a heart using a delivery system, the clip including two arms at an angle relative to one another and a lock having an engaged state and a passively disengaged state, wherein the lock is in the engaged state when the angle is at or below a locking threshold value;

expanding the angle between the arms to a leaflet capture starting angle that is above the locking threshold value such that the lock is in the passively disengaged state;

capturing leaflets of a heart valve by manipulating the clip to trap the leaflets against the arms while the lock remains in the passively disengaged state;

closing the clip to a closure angle by narrowing the angle while the leaflets are trapped against the arms, wherein the lock remains in the passively disengaged state during the closing until the angle falls below the locking threshold value, and wherein the lock automatically transitions from the passively disengaged state to the engaged state without manual actuation of the lock.

17. The method of claim 16, wherein in the engaged state the lock prevents widening of the angle between the arms, and wherein in the passively disengaged state the lock does not prevent widening or narrowing of the angle between the arms.

18. The method of claim 17, wherein the engaged state exists across a range of angles below the locking threshold value, and wherein the closure angle is within the range.

19. A method for implanting a valve repair clip, the method comprising:

introducing the valve repair clip into a heart using a delivery system, the clip including two arms at an angle relative to one another and a lock having an engaged state and a passively disengaged state, wherein the lock is in the engaged state when the angle is at or below a locking threshold value;

expanding the angle between the arms to a leaflet capture starting angle that is above the locking threshold value such that the lock is in the passively disengaged state, wherein in the passively disengaged state the lock permits both widening and narrowing of the angle;

capturing leaflets of a heart valve by manipulating the clip to trap the leaflets against the arms while the lock remains in the passively disengaged state;

closing the clip to a closure angle by narrowing the angle while the leaflets are trapped against the arms, wherein the lock transitions to the engaged state when the angle falls below the locking threshold value, and wherein in the engaged state the lock prevents widening of the angle while permitting narrowing of the angle.

20. The method of claim 19, wherein the closing comprises narrowing the angle through the locking threshold value to cause the lock to transition to the engaged state, and thereafter continuing to narrow the angle to the closure angle while the lock remains in the engaged state.

* * * * *